(12) United States Patent
Retallack et al.

(10) Patent No.: US 9,708,616 B2
(45) Date of Patent: *Jul. 18, 2017

(54) PRODUCTION OF RECOMBINANT PROTEINS UTILIZING NON-ANTIBIOTIC SELECTION METHODS AND THE INCORPORATION OF NON-NATURAL AMINO ACIDS THEREIN

(71) Applicants: Diane M. Retallack, Poway, CA (US); Lawrence C. Chew, San Diego, CA (US); Charles H. Squires, Poway, CA (US)

(72) Inventors: Diane M. Retallack, Poway, CA (US); Lawrence C. Chew, San Diego, CA (US); Charles H. Squires, Poway, CA (US)

(73) Assignee: PFENEX, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/974,897

(22) Filed: Dec. 18, 2015

(65) Prior Publication Data

US 2016/0208268 A1    Jul. 21, 2016

Related U.S. Application Data

(63) Continuation of application No. 13/319,844, filed as application No. PCT/US2010/034201 on May 10, 2010, now Pat. No. 9,243,253.

(Continued)

(51) Int. Cl.
  *C12N 15/00* (2006.01)
  *C12N 15/65* (2006.01)
  (Continued)

(52) U.S. Cl.
  CPC .............. *C12N 15/65* (2013.01); *C12P 21/02* (2013.01); *C12N 15/63* (2013.01); *C12N 15/78* (2013.01)

(58) Field of Classification Search
  CPC ........ C12N 15/65; C12N 15/78; C12N 15/63; C12P 21/02
  See application file for complete search history.

(56) References Cited

U.S. PATENT DOCUMENTS 8,288,127 B2 * 10/2012 Schneider ............ C12N 9/0028
  435/471

OTHER PUBLICATIONS

Schneider et al., auxotrophic markers pyrF and proC can replace antibiotic markers on protein production plasmids in high-cell-density pseudomonas fluorescens fermentation, Biotechnol. Prog. 2005, 21, 343-348.*

* cited by examiner

*Primary Examiner* — Reza Ghafoorian
(74) *Attorney, Agent, or Firm* — Timothy H. Van Dyke; Beusse, Wolter, Sanks & Maire PLLC

(57) ABSTRACT

Provided herein are methods and compositions for expression of a nucleic acid construct comprising nucleic acids encoding a) a recombinant polypeptide, and b) a prototrophy-restoring enzyme in a host cell that is auxotrophic for at least one metabolite. In various embodiments, the host cell is auxotrophic for a nitrogenous base compound or an amino acid. The invention involves introducing an analog into the growth media for the host cell such that the analog is incorporated into the recombinant polypeptide or a nucleic acid coding sequence thereof. In various embodiments, the compositions and methods disclosed herein result in improved recombinant protein expression compared to expression of recombinant protein in an antibiotic selection system, or compared to expression of the recombinant (Continued)

protein in an expression system that lacks a metabolite analog.

17 Claims, 2 Drawing Sheets

Related U.S. Application Data

(60) Provisional application No. 61/177,267, filed on May 11, 2009.

(51) Int. Cl.
*C12P 21/02* (2006.01)
*C12N 15/78* (2006.01)
*C12N 15/63* (2006.01)

PRODUCTION OF RECOMBINANT PROTEINS UTILIZING NON-ANTIBIOTIC SELECTION METHODS AND THE INCORPORATION OF NON-NATURAL AMINO ACIDS THEREIN

CROSS-REFERENCE TO RELATED APPLICATIONS

This application is a continuation of U.S. Ser. No. 13/319,844 filed Nov. 10, 2011, which is a 371 of PCT/US10/034201, filed May 10, 2010, which claims priority to U.S. Provisional Application No. 61/177,267 filed on May 11, 2009 and whose teachings are incorporated herein in their entirety.

FIELD OF THE INVENTION

The present invention provides an improved expression system for the production of recombinant polypeptides utilizing auxotrophic selectable markers and for the incorporation of non-natural amino acids or nitrogenous base compounds into the recombinant polypeptide or coding sequence thereof.

BACKGROUND OF THE INVENTION

The use of bacterial cells to produce protein based therapeutics is increasing in commercial importance. One of the goals in developing a bacterial expression system is the production of high quality target polypeptides quickly, efficiently, and abundantly. An ideal host cell for such an expression system would be able to efficiently utilize a carbon source for the production of a target polypeptide, quickly grow to high cell densities in a fermentation reaction, express the target polypeptide only when induced, and grow on a medium that is devoid of regulatory and environmental concerns.

There are many hurdles to the creation of a superior host cell. First, in order to produce a recombinant polypeptide, an expression vector encoding the target protein must be inserted into the host cell. Many bacteria are capable of reverting back into an untransformed state, wherein the expression vector is eliminated from the host. Such revertants can decrease the fermentation efficiency of the production of the desired recombinant polypeptide.

Expression vectors encoding a target peptide typically include a selection marker in the vector. Often, the selection marker is a gene whose product is required for survival during the fermentation process. Host cells lacking the selection marker, such as revertants, are unable to survive. The use of selection markers during the fermentation process is intended to ensure that only bacteria containing the expression vector survive, eliminating competition between the revertants and transformants and reducing the efficiency of fermentation.

The most commonly used selection markers are antibiotic resistance genes. Host cells are grown in a medium supplemented with an antibiotic capable of being degraded by the selected antibiotic resistance gene product. Cells that do not contain the expression vector with the antibiotic resistance gene are killed by the antibiotic. Typical antibiotic resistance genes include tetracycline, neomycin, kanamycin, and ampicillin. The presence of antibiotic resistance genes in a bacterial host cell, however, presents environmental, regulatory, and commercial problems. For example, antibiotic resistance gene-containing products (and products produced by the use of antibiotic resistance gene) have been identified as potential biosafety risks for environmental, human, and animal health. For example, see M. Droge et al., Horizontal Gene Transfer as a Biosafety issue: A natural phenomenon of public concern, J. Biotechnology. 64(1): 75-90 (17 Sep. 1998); Gallagher, D. M., and D. P. Sinn. 1983. Penicillin-induced anaphylaxis in a patient under hypotensive anaesthesia. Oral Surg. Oral Med. Oral Pathol. 56:361-364; Jorro, G., C. Morales, J. V. Braso, and A. Pelaez. 1996. Anaphylaxis to erythromycin. Ann Allergy Asthma Immunol. 77:456-458; F. Gebhard & K. Smalla, Transformation of *Acinetobacter* sp. strain BD413 by transgenic sugar beet DNA, Appl. & Environ. Microbiol. 64(4):1550-54 (April 1998); T. Hoffinann et al., Foreign DNA sequences are received by a wild type strain of *Aspergillus niger* after co-culture with transgenic higher plants, Curr. Genet. 27(1): 70-76 (December 1994); D K Mercer et al., Fate of free DNA and transformation of the oral bacterium *Streptococcus gordonoii* DL1 by plasmid DNA in human saliva, Appl. & Environ. Microbiol. 65(1):6-10 (January 1999); R. Schubert et al., Foreign (M13) DNA ingested by mice reaches peripheral leukocytes, spleen, and liver via the intestinal wall mucosa and can be covalently linked to mouse DNA, PNAS USA 94:961-66 (Feb. 4, 1997); and A A Salyers, Gene transfer in the mammalian intestinal tract, Curr. Opin. in Biotechnol. 4(3):294-98 (June 1993).

As a result of these concerns, many governmental food, drug, health, and environmental regulatory agencies, as well as many end users, require that antibiotic resistance gene nucleic acid be removed from products or be absent from organisms for use in commerce. In addition, evidence demonstrating clearance of the selection antibiotics from the final product must be provided in order to secure regulatory clearance. The United Kingdom, Canada, France, the European Community, and the United States have all addressed the use of antibiotic resistance genes in foods, animal feeds, drugs and drug production, including recombinant drug production. Clearance of these agents, and especially demonstrating such clearance, is expensive, time consuming, and often only minimally effective.

Because of the concerns inherent in the use of antibiotic resistance genes for selection in the production of recombinant polypeptides, alternative selection methods are needed.

SUMMARY OF THE INVENTION

It has been discovered that recombinant protein production can be improved by selecting as a host cell an organism that is capable of non-antibiotic resistant, auxotrophic selection, and utilizing an analogue of a metabolite for which the host cell is auxotrophic for expression of the recombinant protein. Further, the present inventors have found that after selection of the suitable host cells by the novel "non-antibiotic" process, these cells may be utilized to produce predetermined recombinant proteins that can incorporate non-natural amino acids into the expressed protein.

In accordance with one aspect of the present invention, there is provided a method for producing a recombinant polypeptide of interest. The process includes obtaining a population of cells auxotrophic for a first metabolite and a second metabolite. In one embodiment, the second metabolite is a natural amino acid. In addition, the method includes contacting the population of cells with a first nucleic acid construct comprising an auxotrophic selection marker, wherein the auxotrophic selection marker comprises a first nucleic acid sequence encoding at least one polypeptide active in the biosynthesis of the first metabolite, and wherein expression of the auxotrophic selection marker restores prototrophy for the first metabolite. The population of cells is contacted with a second nucleic acid construct comprising a second nucleic acid sequence encoding the recombinant polypeptide of interest; and a promoter operably attached to the second nucleic acid sequence so as to direct expression of the second nucleic acid sequence. The population of cells is subjected to a first medium lacking the first metabolite under conditions such that transformed cells having restored prototrophy for the first metabolite are obtained. The transformed cells are subjected to a second medium comprising a non-natural amino acid correlating to the second metabolite under conditions such that the second nucleic acid sequence is expressed to produce the recombinant polypeptide of interest having the non-natural amino acid incorporated therein. In the method, the first medium and the second medium may be the same or different. In other words, the first medium may contain the non-natural amino acid, and in such case, may serve as the second medium. Alternatively, the first medium lacks the non-natural amino acid. Once the transformed cells are obtained, then these cells are subjected to a second medium containing a non-natural amino acid.

In accordance with another aspect of the present invention, there is provided a method for producing a recombinant polypeptide of interest. The method comprises: introducing into a host cell that is auxotrophic for a first metabolite required for survival of the host cell a first nucleic acid construct comprising an auxotrophic selection marker. The auxotrophic selection marker comprises a first nucleic acid sequence encoding at least one polypeptide active in the biosynthesis of the first metabolite, and expression of the auxotrophic selection marker restores prototrophy for the first metabolite to the auxotrophic host cell. The method further includes introducing into the host cell: (i) a second nucleic acid construct comprising a second nucleic acid sequence encoding the recombinant polypeptide of interest; (ii) a third nucleic acid sequence encoding an orthogonal tRNA synthetase; (iii) a fourth nucleic acid sequence encoding an orthogonal tRNA interactable with said orthogonal tRNA synthetase; and (iv) a promoter operably attached to the second, third and/or fourth nucleic acid sequences so as to direct expression of the second nucleic acid, third nucleic acid sequence and/or fourth nucleic acid sequence in the auxotrophic host cell. The auxotrophic host cell is subjected to a medium that lacks the first metabolite to obtain transformed cells. The transformed cells are subjected to a media containing a non-natural amino acid under conditions such that the second nucleic acid is expressed to produce the recombinant polypeptide having the non-natural amino acid incorporated therein.

In accordance with yet another aspect of the present invention, there is provided a method for producing a recombinant polypeptide of interest. The method comprises introducing into a host cell that is auxotrophic for a first metabolite a nucleic acid construct. The nucleic acid construct comprises (i) an auxotrophic selection marker, wherein the auxotrophic selection marker comprises a first nucleic acid sequence encoding at least one polypeptide active in the biosynthesis of the first metabolite, and wherein expression of the auxotrophic selection marker restores prototrophy for the first metabolite to the auxotrophic host cell; (ii) a second nucleic acid encoding the recombinant polypeptide of interest; (iii) a third nucleic acid sequence encoding an orthogonal tRNA synthetase; (iv) a fourth nucleic acid sequence encoding a tRNA interactable with the orthogonal tRNA synthetase; and (v) a promoter operably attached to the first, second, third and/or fourth nucleic acid sequences so as to direct expression to at least one thereof. In addition, the method comprises subjecting the auxotrophic host cell to a medium that lacks the first metabolite whereby cells transformed with the nucleic acid construct are obtained. The transformed cells are subjected to a media containing a non-natural amino acid under conditions such that the second nucleic acid is expressed to produce the recombinant polypeptide having the non-natural amino acid incorporated therein.

DETAILED DESCRIPTION OF THE INVENTION

Overview

Figure 1:
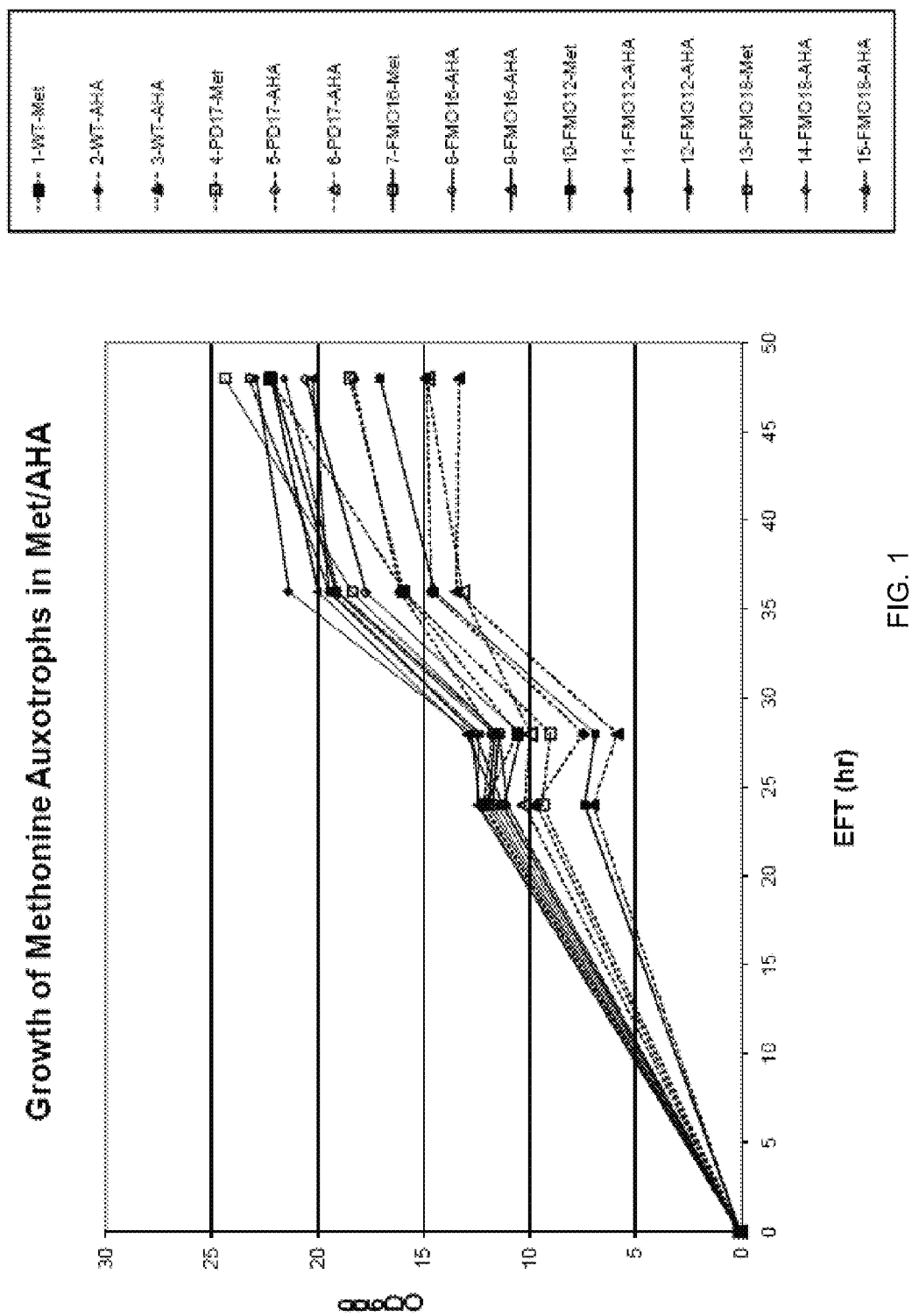
FIG. 1 shows the growth curves for the expression strains examined in this study. Three shake flasks were used for each strain. One flask of each set received methionine as the additive to serve as a control. The other two flasks of the set received AHA for analysis of incorporation of the methionine analogue into expressed IFN-beta protein. Elapsed fermentation time (hours) is indicated on the X-axis and optical density at 600 nm on the Y-axis. At 24 hours of incubation, cells were collected and starved in a medium without added methionine for 0.5 hours. Cells were then resuspended in media containing either methionine or AHA and expression of IFN-beta was induced.

Provided herein are methods for the efficient expression of recombinant polypeptides in an expression system. The methods comprise use of auxotrophic selection markers rather than antibiotic selection markers for plasmid maintenance and selection of transformants. Thereafter, the selected cells, which may also include a second nucleic acid construct comprising a second nucleic acid sequence encoding the recombinant polypeptide of interest, may express the recombinant polypeptide of interest with a non-natural amino acid incorporated therein.

The auxotrophic selection system comprises an auxotrophic host cell that is transformed with one or more expression constructs encoding a polypeptide of interest and a polypeptide capable of restoring prototrophy to the auxotrophic host cell. The "auxotrophic host cell" is any host cell that is deficient in one or more metabolite(s) required for survival of the host cell. In one embodiment, the auxotrophy is a result of genetic modifications to at least one nitrogenous base compound biosynthesis gene, or at least one amino acid biosynthesis gene. A "polypeptide capable of restoring prototrophy" is any polypeptide active in the biosynthesis of the metabolite that is required for survival of said host cell. Thus, auxotrophic host cells are made prototrophic by expression of the heterologous construct comprising the prototrophy-restoring polypeptide.

The present invention further comprises the incorporation of amino acid or nitrogenous base compound analogs into the encoded recombinant polypeptide of interest or a coding sequence encoding the polypeptide of interest, respectively. The methods comprise the addition of one or more analogs of a metabolite for which the auxotrophic host cells are deficient into the growth media for the host cell in a manner in which the analogue is incorporated into the recombinant protein or nitrogenous base compound encoding the protein "Incorporation," as used herein refers to any addition, substitution, replacement, mutation or other modification in which one or more analogue amino acids or nitrogenous base compounds are entered into the target molecule in addition to or as a substitute for a naturally occurring amino acid or nitrogenous base compound.

In various embodiments, use of the metabolite analogue in the presence of an auxotrophic selection system results in improved protein expression relative to expression in an antibiotic selection system, or relative to expression in an antibiotic or auxotrophic selection system in the absence of an analogue.

Protein engineering by means of the introduction of non-natural amino acids is an important approach to the investigation of protein folding, structure, and function as well as the design of novel protein reactivity (Dougherty (2000) Curr Opin Chem Biol 4:645-652). The inventors have realized that presently utilized techniques for recombinant protein expression in the presence of non-natural amino acids may result in lower overall yield of recombinant protein compared to expression in the absence of the non-natural amino acid. While not bound by any particular theory or mechanism, the inventors surmise that the reduced yield may be related to the use of an antibiotic selection marker in the presence of the non-natural amino acid. Having realized a problem inherent in current techniques, the inventors have determined that it would be desirous to develop improved techniques that are easier to control selection of transformed cells, control incorporation of analogues, and which can achieve higher yield of polypeptides of interest. In the present invention, the inventors have developed systems, materials and methods for producing recombinant polypeptides that utilize auxotrophic selection markers, rather than antibiotic selection markers, for plasmid maintenance in order to improve recombinant protein yield in the presence of non-natural amino acids.

In a first embodiment, the present invention comprises obtaining a population of cells auxotrophic for a first metabolite and a second metabolite. Provided herein is a non-limiting list of metabolites. In one embodiment, the second metabolite is a natural amino acid.

The population of cells is contacted with a first nucleic acid construct comprising an auxotrophic selection marker. The auxotrophic selection marker comprises a first nucleic acid sequence encoding at least one polypeptide active in the biosynthesis of the first metabolite. The expression of the auxotrophic selection marker restores prototrophy for the first metabolite.

In some embodiments, the translation system further comprises a culture media containing one or more non-natural amino acids. In still other embodiments, said one or more non-natural amino acids are selected from the group consisting of: azidonorleucine, 3-(1-naphthyl)alanine, 3-(2-naphthyl)alanine, p-ethynyl-phenylalanine, p-propargyl-oxy-phenylalanine, m-ethynyl-phenylalanine, 6-ethynyl-tryptophan, 5-ethynyl-troptophan, (R)-2-amino-3-(4-ethynyl-1H-pyrol-3-yl)propanic acid, p-bromophenylalanine, p-idiophenylalanine, p-azidophenyl-alanine, 3-(6-chloroindolyl)alanine, 3-(6-bromoindolyl)alanine, 3-(5-bromoindolyl)alanine, azidohomoalanine, and p-chlorophenylalanine. In still other embodiments, said modified AARS is selected from the group consisting of: a modified PheRS, a modified TrpRS, a modified TyrRS, and a modified MetRS.

In addition, the population of cells is contacted a second nucleic acid construct comprising a second nucleic acid sequence encoding the recombinant polypeptide of interest. The second nucleic acid sequence also comprises a promoter operably attached to the second nucleic acid sequence so as to direct expression of the second nucleic acid sequence. Typically, but not necessarily, the term operably attached when describing a promoter refers to being arranged on the construct such that it is upstream toward the 5' end of the construct relative to the nucleic acid sequence.

To select transformed cells from a medium, the method comprises subjecting the population of cells to a first medium lacking the first metabolite under conditions such that transformed cells having restored prototrophy for the first metabolite are obtained. In this way, any cells that have not had prototrophy for the first metabolite restored do not survive in the medium.

Once the cells having restored prototrophy for the first metabolite are obtained, the population of cells are subjected to a second medium comprising a non-natural amino acid correlating to the second metabolite under conditions such that the second nucleic acid sequence is expressed to produce the recombinant polypeptide of interest having the non-natural amino acid incorporated therein. The term "correlating" or "correlate(s)" as used herein with respect to describing a non-natural amino acid means that the non-natural amino acid is incorporated into a polypeptide sequence at a codon pertaining to the second metabolite, which is a natural amino acid. For example, the non-natural amino acid (second metabolite) that can bind to a tRNA pertaining to a natural amino acid correlates with the natural amino acid.

In the method, the first medium and the second medium may be the same or different. In one embodiment, the first medium and the second medium are the same. By "the same," it is meant that both media contain the desired non-natural amino acid. In one embodiment, the first medium and second medium are different. By "different," it is meant that one of the media contains the desired non-natural amino acid and the other media does not.

In another embodiment, there is a method for producing a recombinant polypeptide of interest. The method comprises introducing into a host cell that is auxotrophic for a first metabolite required for survival of the host cell a first nucleic acid construct comprising an auxotrophic selection marker. The auxotrophic selection marker comprises a first nucleic acid sequence encoding at least one polypeptide active in the biosynthesis of the first metabolite. The expression of the auxotrophic selection marker restores prototrophy for the first metabolite to the auxotrophic host cell.

The method also includes introducing a second nucleic acid construct comprising a second nucleic acid sequence encoding the recombinant polypeptide of interest into the host cell.

Further, a third nucleic acid sequence encoding an orthogonal tRNA synthetase is introduced into the host cell along with a promoter operably attached to the second and third nucleic acid sequences so as to direct expression of the second nucleic acid and third nucleic acid sequence in the auxotrophic host cell. Moreover, the second nucleic acid construct comprises a fourth nucleic acid sequence encoding an orthogonal tRNA that can interact with the orthogonal tRNA synthetase.

The auxotrophic host cell is subjected to a medium that lacks the first metabolite thereby enabling selection of transformed cells. The transformed cells are grown under conditions such that the third and fourth nucleic acid sequences are expressed to produce an orthogonal tRNA synthetase and orthogonal tRNA, respectively. The transformed cells are subjected to a medium comprising a non-natural amino acid that is interactable with the orthogonal tRNA. The orthogonal tRNA synthetase and the orthogonal tRNA interact to facilatate the incorporation of the interactable non-natural amino acid into the recombinant polypeptide of interest during expression to produce the recombinant polypeptide having the non-natural amino acid incorporated therein.

According to another embodiment, the first, second, third and fourth nucleic acid sequences described in the preceding paragraphs are all provided on the same construct, as opposed to a first and second construct. In an alternative embodiment, the first, second, third and fourth nucleic acid sequences are on separate constructs.

DEFINITIONS

As used herein, the term "percent total cell protein" means the amount of protein or peptide in the host cell as a percentage of aggregate cellular protein.

The term "operably attached," as used herein, refers to any configuration in which the transcriptional and any translational regulatory elements are covalently attached to the encoding sequence in such disposition(s), relative to the coding sequence, that in and by action of the host cell, the regulatory elements can direct the expression of the coding sequence.

The term "auxotrophic," as used herein, refers to a cell which has been modified to eliminate or reduce its ability to produce a specific substance required for growth and metabolism.

The term "prototrophy," as used herein, refers to a cell that is capable of producing a specific substance required for growth and metabolism.

The term "non-natural amino acid" as used herein, refers to an amino acid that is different from the twenty naturally occurring amino acids (alanine, arginine, glycine, asparagine, aspartic acid, cysteine, glutamine, glutamic acid, serine, threonine, histidine, lysine, methionine, proline, valine, isoleucine, leucine, tyrosine, tryptophan, phenylalanine) in its side chain functionality. Such different side chain functionalities may include, but are not limited to, halogens, unsaturated hydrocarbons, heterocycles, silicon, organometallic units. These additional side chains may improve the stability of the folded structure of proteins without requiring sequence modifications. A non-limiting list of non-natural amino acids that may be used in accordance with the teachings herein includes, but is not limited to, azidonorleucine, 3-(1-naphthyl)alanine, 3-(2-naphthyl)alanine, p-ethynyl-phenylalanine, p-propargly-oxy-phenylalanine, m-ethynyl-phenylalanine, 6-ethynyl-tryptophan, 5-ethynyl-troptophan, (R)-2-amino-3-(4-ethynyl-1H-pyrol-3-yl)propanic acid, p-bromophenylalanine, p-idiophenylalanine, p-azidophenylalanine, 3-(6-chloroindolyl)alanine, 3-(6-bromoindolyl)alanine, 3-(5-bromoindolyl)alanine, azidohomoalanine, and p-chlorophenylalanine. In still other embodiments, said modified AARS is selected from the group consisting of: a modified PheRS, a modified TrpRS, a modified TyrRS, and a modified MetRS.

The term "introduce(s)(ed)(ing)" as used herein in relation to nucleic acid sequences, or constructs comprising same, refers to contact and uptake of an exogenous sequence and/or construct into a cell. "Introducing" refers to the act of introducing. "Transformation" is a type of introduction and typically refers to the uptake and stable replication of a plasmid into a cell, or the uptake of a linear nucleic acid sequence or construct into a cell whereby the exogenous sequence or construct is stably inserted into the genome of the transformed cell.

The term "nucleic acid construct" as used herein refers to a polynucleotide having two or more nucleic acid sequence elements having separate purposes or functions. In certain embodiments, a nucleic acid construct may be provided in the form of a plasmid, or other suitable vector for introduction to a cell.

Auxotrophic Selection Systems

Auxotrophic selection markers have been utilized as an alternative to antibiotic selection in some systems. For example, auxotrophic markers have been widely utilized in yeast, due largely to the inefficiency of antibiotic resistance selection markers in these host cells. See, for example, J T Pronk, (2002) "Auxotrophic yeast strains in fundamental and applied research," App. & Environ. Micro. 68(5): 2095-2100; Boeke et al., (1984) "A positive selection for mutants lacking orotodine-5'-phosphate decarboxylase activity in yeast; 5-fluoro-orotic acid resistance," Mol. Gen. Genet. 197: 345-346; Botstein & Davis, (1982) "Principles and practice of recombinant DNA research with yeast," p. 607-636, in J N Strathern, E W Jones. And J R Broach (ed.), The molecular biology of the yeast *Saccharomyces cerevisiae*, Metabolism and gene expression, Cold Spring Harbor Laboratory Press, Cold Spring Harbor, N.Y.; Cost & Boeke, (1996) "A useful colony color phenotype associated with the yeast selectable/counter selectable marker MET15," Yeast 12: 939-941.

Auxotrophic marker selection in bacteria has also previously been described. See, for example, U.S. Pat. Nos. 4,920,048, 5,691,185, 6,291,245, 6,413,768, and 6,752,994; U.S. Patent Publication No. 20050186666; Struhl et al. (1976) PNAS USA 73; 1471-1475; MacCormick et al., (1995) FEMS Microbiol. Lett. 127:105-109; Dickely et al. (1995) Mol. Microbiol. 15:839-847; Sorensen et al. (2000) Appl. Environ. Microbiol 66:1253-1258; and Fiedler & Skerra (2001) Gene 274: 111-118.

In an aspect of the present invention, a population of host cells is obtained or otherwise provided, which is auxotrophic for at least one metabolite. It is contemplated that the auxotrophic host cells may be provided from a suitable commercial source or, in one embodiment, may have been genetically modified to induce auxotrophy for at least one metabolite. The genetic modification can be to a gene or genes encoding an enzyme that is operative in a metabolic pathway, such as an anabolic biosynthetic pathway or catabolic utilization pathway. Preferably, the host cell has all operative genes encoding a given biocatalytic activity deleted or inactivated in order to ensure removal of the biocatalytic activity.

One or more than one metabolic activity may be selected for knock-out or replacement. In the case of native auxotrophy(ies), additional metabolic knockouts or replacements can be provided. Where multiple activities are selected, the auxotrophy-restoring selection markers can be of a biosynthetic-type (anabolic), of a utilization-type (catabolic), or may be chosen from both types. For example, one or more than one activity in a given biosynthetic pathway for the selected compound may be knocked-out; or more than one activity, each from different biosynthetic pathways, may be knocked-out. The corresponding activity or activities are then provided by at least one recombinant vector which, upon transformation into the cell, restores prototrophy to the cell.

Compounds and molecules whose biosynthesis or utilization can be targeted to produce auxotrophic host cells include: lipids, including, for example, fatty acids; mono- and disaccharides and substituted derivatives thereof, including, for example, glucose, fructose, sucrose, glucose-6-phosphate, and glucuronic acid, as well as Entner-Doudoroff and Pentose Phosphate pathway intermediates and products; nucleosides, nucleotides, dinucleotides, including, for example, ATP, dCTP, FMN, FAD, NAD, NADP, nitrogenous bases, including, for example, pyridines, purines, pyrimidines, pterins, and hydro-, dehydro-, and/or substituted nitrogenous base derivatives, such as cofactors, for example, biotin, cobamamide, riboflavine, thiamine; organic acids and glycolysis and citric acid cycle intermediates and products, including, for example, hydroxyacids and amino acids; storage carbohydrates and storage poly(hydroxyalkanoate) polymers, including, for example, cellulose, starch, amylose, amylopectin, glycogen, poly-hydroxybutyrate, and polylactate.

In one embodiment, the biocatalytic activity(ies) knocked out to produce the auxotrophic host cell is selected from the group consisting of: the lipids; the nucleosides, nucleotides, dinucleotides, nitrogenous bases, and nitrogenous base derivatives; and the organic acids and glycolysis and citric acid cycle intermediates and products. Preferably, the biocatalytic activity(ies) knocked out is selected from the group consisting of: the nucleosides, nucleotides, dinucleotides, nitrogenous bases, and nitrogenous base derivatives; and the organic acids and glycolysis and citric acid cycle intermediates and products. More preferably, the biocatalytic activity(ies) knocked out is selected from the group consisting of: the pyrimidine nucleosides, nucleotides, dinucleotides, nitrogenous bases, and nitrogenous base derivatives; and the amino acids.

A given transgenic host cell may use one or more than one selection marker or selection marker system. For example, one or more biosynthesis selection marker(s) or selection marker system(s) according to the present invention may be used together with each other, and/or may be used in combination with a utilization-type selection marker or selection marker system according to the present invention. In any one of these prototrophy-enabling embodiments, the host cell may also contain one or more non-auxotrophic selection marker(s) or selection marker system(s). Examples of non-auxotrophic selection marker(s) and system(s) include, for example: toxin-resistance marker genes such as antibiotic-resistance genes that encode an enzymatic activity that degrades an antibiotic; toxin-resistant marker genes, such as, for example, imidazolinone-resistant mutants of acetolactate synthase ("ALS;" EC 2.2.1.6) in which mutation(s) are expressed that make the enzyme insensitive to toxin-inhibition exhibited by versions of the enzyme that do not contain such mutation(s). The compound(s) may exert this effect directly; or the compound(s) may exert this effect indirectly, for example, as a result of metabolic action of the cell that converts the compound(s) into toxin form or as a result of combination of the compound(s) with at least one further compound(s).

Host cell-operative genes encoding such marker enzymes can be obtained from the host cell strain chosen for construction of the knock-out cell, from related strains, or from other organisms, and may be used in native form or modified (e.g., mutated or sequence recombined) form. For example, a DNA coding sequence for an enzyme exhibiting the knocked out biocatalytic activity may be obtained from one or more organisms and then operably attached to DNA regulatory elements operative within the host cell. In specific, all of the chosen host cell's intracellular genes that encode a selected enzymatic activity are knocked-out; the knock-out host is then transformed with a vector containing at least one operative copy of a native or non-native gene encoding an enzyme exhibiting the activity lost by the knockout.

The genes encoding such enzymes can be selected and obtained through various resources available to one of ordinary skill in the art. These include the nucleotide sequences of enzyme coding sequences and species-operative DNA regulatory elements. Useful on-line InterNet resources include, e.g.: (1) the ExPASy proteomics facility (see the ENZYME and BIOCHEMICAL PATHWAYS MAPS features) of the Swiss Institute of Bioinformatics (Batiment Ecole de Pharmacie, Room 3041; Universitde Lausanne; 1015 Lausanne-Dorigny; Switzerland) available at, e.g., us.expasy.org/; and (2) the GenBank facility and other Entrez resources (see the PUBMED, PROTEIN, NUCLEOTIDE, STRUCTURE, GENOME, et al. features) offered by the National Center for Biotechnology Information (NCBI, National Library of Medicine, National Institutes of Health, U.S. Dept. of Health & Human Services; Building 38A; Bethesda, Md., USA) and available at www.ncbi.nlm.nih.gov/entrez/guery.fcgi.

The selected coding sequence may be modified by altering the genetic code thereof to match that employed by the host cell utilized in the system, and the codon sequence thereof may be enhanced to better approximate that employed by the host. Genetic code selection and codon frequency enhancement may be performed according to any of the various methods known to one of ordinary skill in the art, e.g., oligonucleotide-directed mutagenesis. Useful on-line InterNet resources to assist in this process include, e.g.: (1) the Codon Usage Database of the Kazusa DNA Research Institute (2-6-7 Kazusa-kamatari, Kisarazu, Chiba 292-0818 Japan) and available at www.kazusa.or.jp/codon/; and (2) the Genetic Codes tables available from the NCBI Taxonomy database at www.ncbi.nlm.nih.gov/Taxonomy/Utils/wprintgc.cgi?mode=c. For example, *Pseudomonas* species are reported as utilizing Genetic Code Translation Table 11 of the NCBI Taxonomy site, and at the Kazusa site as exhibiting the codon usage frequency of the table shown at www.kazusa.or.jp/codon/cgibin/.

Biosynthetic Nucleoside and Nitrogenous Base Selection Markers

In one embodiment, a biosynthetic enzyme involved in anabolic metabolism can be chosen as the auxotrophic selection marker. In particular, the biosynthetic enzyme can be selected from those involved in biosynthesis of the nucleosides, nucleotides, dinucleotides, nitrogenous bases, and nitrogenous base derivatives, which are collectively referred to herein as base selection markers.

In a particular embodiment at least one purine-type biosynthetic enzyme can be chosen as an auxotrophic selection marker. Such purine biosynthetic enzymes include, for example, adenine phosphoribosyltransferases, adenylosuccinate lyases, adenylosuccinate synthases, GMP synthases, IMP cyclohydrolases, IMP dehydrogenases, phosphoribosylamine-glycine ligases, phosphoribosyl-aminoimidazole-carboxa-mide formyltransferases, phosphoribosylaminoimidazole carboxylases, phosphoribosyl aminoimidazolesuccinocarboxamide synthases, phosphoribosyl-formylglycinamidine cyclo ligases, phosphoribosyl-formylglycinamidine synthases, phosphoribosyl-glycinamide formyltransferases, ribose-phosphate diphosphokinases, and ribose-5-phosphate-ammonia ligases.

In another particular embodiment, a pyrimidine-type biosynthetic enzyme can be chosen as an auxotrophic selection marker. Such pyrimidine-type biosynthetic include enzymes involved in biosynthesis of UMP, such as carbamate kinase (EC 2.7.2.2), carbamoyl-phosphate synthase (EC 6.3.5.5), aspartate carbamoyltransferase (EC 2.1.3.2), dihydroorotase (EC 3.5.2.3), dihydroorotate dehydrogenase (EC 1.3.3.1), orotate phosphoribosyltransferase ("OPRT;" EC 2.4.2.10), and orotidine-5'-phosphate decarboxylase ("ODCase;" EC 4.1.1.23).

Examples of genes encoding pyrimidine-type biosynthetic enzymes are well known. In the case of bacterial synthesis of UMP, examples of useful genes include: arcC genes, encoding carbamate kinases; carA and carB genes, collectively encoding carbamoyl-phosphate synthases; pyrB genes, encoding aspartate carbamoytransferases; pyrC genes, encoding dihydroorotases; pyrD genes, singly or collectively encoding dihydroorotate dehydrogenases; pyrE genes encoding orotate phosphoribosyltransferases; and pyrF genes, encoding orotidine-5'-phosphate decarboxylases.

In a particular embodiment, an expression system according to the present invention will utilize a pyrF auxotrophic selection marker gene. pyrF genes encode ODCase, an enzyme required for the bacterial pyrimidine nucleotide biosynthesis pathway, by which the cell performs de novo synthesis of pyrimidine nucleotides proper (UTP, CTP), as well as pyrimidine deoxynucleotides (dTTP, dCTP). The pathway's initial reactants are ATP, an amino group source (i.e. ammonium ion or L-glutamine), and a carboxyl group source (i.e. carbon dioxide or bicarbonate ion); the pathway's ultimate product is dTTP, with dCTP, UTP, and CTP also being formed in the process. Specifically, the bacterial de novo pyrimidine nucleotide biosynthesis pathway begins with the formation of carbamoyl phosphate. Carbamoyl phosphate is synthesized either: (a) by action of carbamate kinase (EC 2.7.2.2), encoded by the arcC gene; or, more commonly, (b) by action of the glutamine-hydrolyzing, carbamoyl-phosphate synthase (EC 6.3.5.5), whose small and large subunits are encoded by the carA and carB genes, respectively. Carbamoyl phosphate is then converted to UDP by the following six-step route: 1) conversion of carbamoyl phosphate to N-carbamoyl-L-aspartate, by aspartate carbamoyltransferase (EC 2.1.3.2), encoded by pyrB; then 2) conversion thereof to (S)-dihydroorotate, by dihydroorotase (EC 3.5.2.3), encoded by pyrC; then 3) conversion thereof to orotate, by dihydroorotate dehydrogenase (EC 1.3.3.1), encoded by pyrD gene(s); then 4) conversion thereof to orotidine-5'-monophosphate ("OMP"), by orotate phosphoribosyltransferase ("OPRT;" EC 2.4.2.10), encoded by pyrE; and then 5) conversion thereof to uridine-5'-monophosphate ("UMP"), by orotidine-5'-phosphate decarboxylase ("ODCase;" EC 4.1.1.23), encoded by pyrF. The UMP is then utilized by a variety of pathways for synthesis of pyrimidine nucleotides (UTP, CTP, dTTP, dCTP), nucleic acids, nucleoproteins, and other cellular metabolites.

In bacteria in which one or more of the carA, carB, or pyrB-pyrF genes has become inactivated or lost, or mutated to encode a non-functional enzyme, the cell can still thrive if uracil is added to the medium, provided that the cell contains a functioning uracil salvage pathway. Most bacteria contain a native uracil salvage pathway, including the Pseudomonads and related species. In a uracil salvage pathway, the cell imports and converts exogenous uracil into UMP, to synthesize the required pyrimidine nucleotides. In this, uracil is reacted with 5-phosphoribosyl-1-pyrophosphate to form UMP, by the action of either uracil phosphoribosyltransferase (EC 2.4.2.9), encoded by the upp gene, or by the bifunctional, pyrimidine operon regulatory protein ("pyrR bifunctional protein"), encoded by pyrR. The resulting UMP is then converted to UDP, and then the subsequent pyrimidine nucleotides, as described above.

Consequently, a pyrF(−) host cell can be maintained on uracil-containing medium. After a pyrF gene-containing DNA construct is transfected into the pyrF(−) cell and expressed to form a functioning ODCase enzyme, the resulting combined pyrF(+) plasmid-host cell system can be maintained in a medium lacking uracil.

The coding sequence of the pyrF gene for use in a host cell of interest can be provided by any gene encoding an orotidine-5'-phosphate decarboxylase enzyme ("ODCase") (or homolog thereof), provided that the coding sequence can be transcribed, translated, and otherwise processed by the selected host cell to form a functioning ODCase. The pyrF coding sequence may be a native sequence, or it may be an engineered sequence resulting from, for example, application of one or more sequence-altering, sequence-combining, and/or sequence-generating techniques known in the art. Before use as part of a pyrF selection marker gene, the selected coding sequence may first be improved or optimized in accordance with the genetic code and/or the codon usage frequency of a selected host cell. Expressible coding sequences will be operably attached to a transcription promoter capable of functioning in the chosen host cell, as well as all other required transcription and translation regulatory elements. A native coding sequence for a pyrF gene as described above may be obtained from a bacterium or from any other organism, provided that it meets the above-described requirements.

In one embodiment, the pyrF coding sequence is isolated from the host cell in which it is intended to be used as a selection marker. The entire pyrF gene (including the coding sequence and surrounding regulatory regions) can be isolated therefrom.

In an alternate embodiment, an expression system according to the present invention will utilize a thyA auxotrophic selection marker gene. The thyA genes encode thymidylate synthase (EC 2.1.1.45), an enzyme required for the bacterial pyrimidine nucleotide biosynthesis pathway. Since DNA contains thymine (5-methyluracil) as a major base instead of uracil, the synthesis of thymidine monophospate (dTMP or thymidylate) is essential to provide dTTP (thymidine triphosphate) needed for DNA replication together with dATP, dGTP, and dCTP. Methylation of dUMP by thymidylate synthase utilizing 5,10-methylenetetrahydrofolate as the source of the methyl group generates thymidylate. Thymidylate synthesis can be interrupted, and consequently the synthesis of DNA arrested, by the removal, inhibition, or disruption of thymidylate synthase.

In bacteria in which the thyA gene has become inactivated or lost, or mutated to encode a non-functional enzyme, the cell can still thrive if exogenous thymidine is added to the medium.

In Pseudomonas fluorescens, the addition of an E. coli tdk gene, encoding thymidine kinase, is required for survival on exogenous thymidine. Therefore, prior to selection, a plasmid comprising a tdk gene can be used to transform thyA(−) P. fluorescens host cells, generating a thyA(−)/ptdk cell, allowing survival on a thymidine containing medium. Alternatively, a tdk gene producing a functional thymidylate synthase enzyme capable of utilizing exogenous thymidine in *Pseudomonas fluorescens* can be inserted into the genome, producing a thyA(−)/tdk(+) host cell. After a thyA gene-containing DNA construct is transfected into the thyA (−)/ptdk cell and expressed to form a functioning thymidylate synthase enzyme, the resulting combined thyA(+) plasmid-host cell system can be maintained in a medium lacking thymidine.

Biosynthetic Amino Acid Selection Markers

In an alternative embodiment, the biosynthetic enzyme involved in anabolic metabolism chosen as the auxotrophic selection marker can be selected from those involved in the biosynthesis of amino acids. In particular embodiments, the biosynthetic amino acid enzymes are selected from the group consisting of enzymes active in the biosynthesis of: the Glutamate Family (Glu; Gln, Pro, and Arg); the Aspartate Family (Asp; Asn, Met, Thr, Lys, and Ile); the Serine Family (Ser; Gly and Cys); the Pyruvate Family (Ala, Val, and Leu); the Aromatic Family (Trp, Phe, and Tyr); and the Histidine Family (His). Examples of genes and enzymes involved in these biosynthetic pathways include: the Glutamate Family member arg, gdh, gln, and, pro genes, including, for example, argA-argH, gdhA, glnA, proA, proC; the Aspartate Family member asd, asn, asp, dap, lys, met, and thr genes, including, for example, asnA, asnB, aspC, dapA, dapB, dapD-dapF, lysA, lysC, metA-metC, metE, metH, metL, thrA-thrC; the Serine Family member cys, gly, and ser genes, including, for example, cysE, cysK, glyA, serA-serC; the Aromatic Family member aro, phe, trp, and tyr genes, including, for example, aroA-aroH, aroK, aroL, trpAtrpE, tyrA, and tyrB; and the Histidine Family member his genes, including hisA-hisD, hisF-hisH.

In a further particular embodiment, the auxotrophic selection marker can be selected from enzymes involved in the biosynthesis of members of the Glutamate Family. Examples of useful Glutamate Family auxotrophic selection markers include the following, listed with representative examples of their encoding genes: argA, encoding N-acetylglutamate synthases, amino acid acetyltransferases; argB, encoding acetylglutamate kinases; argC, encoding N-acetyl-gammaglutamylph-osphate reductases; argD, encoding acetylornithine delta-aminotransferases-; argE, encoding acetylornithine deacetylases; argF and argI, encoding ornithine carbamoyltransferases; argG, encoding argininosuccinate synthetases; argH, encoding argininosuccinate lyases; gdhA, encoding glutamate dehydrogenases; glnA, encoding glutamine synthetases; proA, encoding gamma-glutamyl-phosphate reductases; proB, encoding gamma-glutamate kinases; and proC, encoding pyrroline-5-carboxylate reductases.

In one embodiment, an amino acid biosynthesis selection marker gene can be at least one member of the proline biosynthesis family, in particular proA, proB, or proC. In a particular embodiment, the proline biosynthesis selection marker gene can comprise a proC gene. proC genes encode an enzyme catalyzing the final step of the proline biosynthesis pathway. In bacteria, the proline (i.e. L-proline) biosynthesis pathway comprises a three-enzyme process, beginning with L-glutamic acid. The steps of this process are: 1) conversion of L-glutamic acid to L-glutamyl-5-phosphate, by glutamate-5-kinase ("GK;" EC 2.7.2.11), encoded by proB; then 2a) conversion thereof to L-glutamate-5-semialdehyd-e, by glutamate-5-semialdehyde dehydrogenase (EC 1.2.1.41), also known as glutamyl-5-phosphate reductase ("GPR"), encoded by proA, followed by 2b) spontaneous cyclization thereof to form 0.1-pyrroline-5-carboxylate; and then 3) conversion thereof to L-proline, by Δ1-pyrroline-5-car-boxylate reductase ("P5CR;" EC 1.5.1.2), encoded by proC. In most bacteria, proC encodes the P5CR subunit, with the active P5CR enzyme being a homo-multimer thereof.

Utilization Selection Markers

In one embodiment, an enzyme involved in the catabolic utilization of metabolites can be chosen as the auxotrophic selection marker. In particular, the enzymes can be selected from those involved in the utilization of a carbon source. Examples of such enzymes include, for example, sucrases, lactases, maltases, starch catabolic enzymes, glycogen catabolic enzymes, cellulases, and poly(hydroxyalkanoate)depolymerases. If the bacterial host cell exhibits native catabolic activity of the selected type, it can be knocked-out before transformation with the prototrophy-restoring vector. Bacteria exhibiting native auxotrophy for these compounds can also be used in their native state for such transformation. In those embodiments in which a compound not importable or diffusible into the cell can be selected and supplied to the medium, the prototrophy restoring or prototrophy-enabling enzyme(s) can be secreted for use. In that case, the secreted enzyme(s) can degrade the compound extracellularly to produce smaller compounds, for example glucose, that are diffusible or importable into the cell, by selecting or designing the coding sequence of the enzyme(s) to include a coding sequence for a secretion signal peptide operative within the chosen host cell. In these embodiments, the prototrophy-restorative gene can be selected or be engineered to include a coding sequence for a secretion signal peptide operative within the chosen host cell to obtaining transport of the enzyme across the cytoplasmic membrane. In either of these embodiments, or those in which the selected compound is importable or diffusible into the cell, the cell will be grown in medium supplying no other carbon source apart from the selected compound.

In a carbon-source-utilization-based marker system, every prototrophy-restorative or prototrophy-enabling carbon-source utilization enzyme can be involved in utilization of only one carbon source. For example, two genes from the same catabolic pathway may be expressed together on one vector or may be co-expressed separately on different vectors in order to provide the prototrophy. Specific examples of such multi-gene carbon-source-utilization-based marker systems include, for example, the use of glycogen as the sole carbon source with transgenic expression of both a glycogen phosphorylase and an (alpha-1,4)glucantransferase; and the use of starch as the sole carbon source with transgenic expression of both an alpha-amylase, and an alpha(1->6) glucosidase. However, the selected single- or multi-gene carbon-source marker system can be used simultaneously with other types of marker system(s) in the same host cell, provided that the only carbon source provided to the cell is the compound selected for use in the carbon-source catabolic selection marker system.

Other examples of useful enzymes for biochemical-utilization-type activities are well known in the art, and can include racemases and epimerases that are capable of converting a non-utilizable D-carbon source, supplied to the cell, to a nutritive L-carbon source. Examples of these systems include, for example: a D-acid or a D-acyl compound used with trangenic expression of the corresponding racemase; and lactate used with transgenically expressed lactate racemase.

Similarly, where an amino acid biosynthetic activity has been selected for use in the marker system, the auxotrophy may also be overcome by supplying the cell with both a non-utilizable R-amino acid and an R-amino acid racemase or epimerase (EC 5.1.1) that converts the R-amino acid into the corresponding L-amino acid for which the cell is auxotrophic.

Trait Stacking

A plurality of phenotypic changes can also be made to a host cell, before or after insertion of an auxotrophic selection marker gene, for target gene expression, according to the present invention. For example, the cell can be genetically engineered, either simultaneously or sequentially, to exhibit a variety of enhancing phenotypic traits. This process is referred to as "trait stacking." For example, a pyrF deletion may be present as one such phenotypic trait. In such a strain, a pyrF gene, according to the present invention, can be used on a suicide vector as both a selectable marker and a counterselectable marker (in the presence of 5'-fluoroorotic acid) in order to effect a cross-in/cross-out allele exchange of other desirable traits, Thus, a pyrF gene according to the present invention may be used in a process for "trait stacking" a host cell. In such a process, a suicide vector containing such a pyrF gene can be transformed into the host cell strain in a plurality of separate transformations; in each such procedure the re-establishment of the pyrF phenotype can be used to create, ad infinitum, subsequent genetically-enhancing phenotypic change. Thus, not only can the pyrF gene itself provide a trait, it can be used to obtain additional phenotypic traits in a process of trait-stacking.

In one embodiment, the present invention provides auxotrophic host cells that have been further genetically modified to induce additional auxotrophies. For example, a pyrF(−) auxotroph can be further modified to inactivate another biosynthetic enzyme present in an anabolic or catabolic pathway, such as through the inactivation of a proC gene or a thyA gene. In this way, multiple auxotrophies in the host cell can be produced.

In another embodiment, genetic alterations can be made to the host cell in order to improve the expression of recombinant polypeptides in the host cell. Further modifications can include genetic alterations that allow for a more efficient utilization of a particular carbon source, thereby optimizing the overall efficiency of the entire fermentation.

In one particular embodiment, auxotrophic host cells are further modified by the insertion of a lad containing transgene into the host chromosome. Preferably, the lad transgene, or derivate thereof, is other than part of a whole or truncated structural gene containing PlacI-lacI-lacZYA construct.

Amino Acid and Nitrogenous Base Analogues

The present invention encompasses incorporation into the recombinant polypeptide expressed by the auxotrophic host cell of one or more analogues of the metabolite for which the host cell is auxotrophic. In various embodiments, the analogue of the metabolite is a non-natural amino acid or a non-natural nitrogenous base compound. One of skill in the art would recognize which analogues would substitute for the various metabolites described herein and known in the art.

Amino acid analogue," "non-canonical amino acid," "non-natural amino acid," "modified amino acid," "non-natural AARS substrate," "non-natural AARS substrate," "non-standard amino acid," "non-natural amino acid," and the like may all be used interchangeably, and is meant to include all amino acid-like compounds that are similar in structure and/or overall shape to one or more of the twenty L-amino acids commonly found in naturally occurring proteins (Ala or A, Cys or C, Asp or D, Glu or E, Phe or F, Gly or G, His or H, Ile or I, Lys or K, Leu or L, Met or M, Asn or N, Pro or P, Gln or Q, Arg or R, Ser or S, Thr or T, Val or V, Trp or W, Tyr or Y, as defined and listed in WIPO Standard ST.25 (1998), Appendix 2, Table 3). Amino acid analogs can also be natural amino acids with modified side chains or backbones. Amino acids can also be naturally occurring amino acids in D-, rather than L-form. In some embodiments, the non-natural amino acid comprises a carbonyl group, an acetyl group, an aminooxy group, a hydrazine group, a hydrazide group, a semicarbazide group, an azide group, or an alkyne group.

Likewise, nitrogenous base analogue," "non-natural nitrogenous base," "modified nitrogenous base," "non-standard nitrogenous base," "non-natural nitrogenous base," and the like may all be used interchangeably, and is meant to include all nitrogenous base-like compounds that are similar in structure and/or overall shape to one or more of the five nitrogenous bases commonly found in naturally occurring nucleic acid molecules.

Analogues of amino acids and nitrogenous base compounds are known in the art. Non-limiting examples include pyrazolo[3,4-d]pyrimidines, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-propynyl uracil and cytosine, 6-azo uracil, cytosine and thymine, 5-uracil (pseudouracil), 4-thiouracil, 8-halo (e.g., 8-bromo), 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, deazaguanine, 7-deazaguanine, 3-deazaguanine, deazaadenine, 7-deazaadenine, 3-deazaadenine, pyrazolo[3,4-d]pyrimidine, imidazo[1,5-a]1,3,5 triazinones, 9-deazapurines, imidazo[4,5-d]pyrazines, thiazolo[4,5-d]pyrimidines, pyrazin-2-ones, 1,2,4-triazine, pyridazine, 1,3,5 triazine, iodotyrosine, azidohomoalanine, homoproparglyglycine, para-bromophenylalanine, para-iodophenylalanine, azidophenylalanine, acetylphenylalanine, ethynylephenylalanine, azidonorleucine, 3-(1-naphthyl)alanine, 3-(2-naphthyl)alanine, p-ethynyl-phenylalanine, p-propargly-oxyphenylalanine, m-ethynyl-phenylalanine, 6-ethynyl-tryptophan, 5-ethynyl-tryptophan, (R)-2-amino-3-(4-ethynyl-1H-pyrol-3-yl)propanic acid, p-bromophenylalanine, p-idiophenylalanine, p-azidophenylalanine, 3-(6-chloroindolyl)alanine, 3-(6-bromoindoyl)alanine, 3-(5-bromoindolyl)alanine, azidohomoalanine, and p-chlorophenylalanine.

Modifications to Induce Auxotrophism

A host cell selected for use in an expression system according to the present invention can be deficient in its ability to express any functional biocatalyst exhibiting the selected auxotrophic activity. For example, where an orotidine-5'-phosphate decarboxylase activity is selected, the host cell can be deficient in its ability to express a) any pyrF gene product (i.e. any functional ODCase enzyme), and b) any effective replacement therefore (i.e. any other biocatalyst having ODCase activity). In one embodiment, the host cell will be made biocatalytically-deficient for the selected activity by altering its genomic gene(s) so that the cell cannot express, from its genome, a functional enzyme involved in the targeted auxotrophy (i.e. ODCase). In other words, the prototrophic cell (activity(+) cell) will become auxotrophic through the "knock-out" of a functional enzymatic encoding gene involved in the targeted prototrophic pathway (i.e. an activity(−) cell). This alteration can be done by altering the cell's genomic coding sequence(s) of the gene(s) encoding the selected activity(ies). In one embodiment, the coding sequence alteration(s) will be accomplished by introducing: insertion or deletion mutation(s) that change the coding sequence reading frame(s); substitution or inversion mutations that alter a sufficient number of codons; and/or deletion mutations that delete a sufficiently large group of contiguous codons there from capable of producing a non-functional enzyme.

In one embodiment in which the host cell strain has also provided the auxotrophic gene(s) for use as selection marker(s) therein, preferably each of the selected gene's transcription promoter and/or transcription terminator element(s) can also be inactivated by introduction of mutation(s), including deletion mutations. For example, the transcription element inactivation can be optionally performed in addition to the coding sequence alteration(s) described above. In one embodiment in which the host cell strain has also provided the auxotrophic selection marker gene(s), all of the selected gene(s)'s DNA can be deleted from the host cell genome.

Such knock-out strains can be prepared according to any of the various methods known in the art as effective. For example, homologous recombination vectors containing homologous targeted gene sequences 5' and 3' of the desired nucleic acid deletion sequence can be transformed into the host cell. Ideally, upon homologous recombination, a desired targeted enzymatic gene knock-out can be produced. One of skill in the art will further recognize that a variety of auxotrophic cell lines are commercially available.

Specific examples of gene knock-out methodologies include, for example: Gene inactivation by insertion of a polynucleotide has been previously described. See, e.g., D L Roeder & A Collmer, Marker-exchange mutagenesis of a pectate lyase isozyme gene in *Erwinia chrysanthemi*, J Bacteriol. 164(1):51-56 (1985). Alternatively, transposon mutagenesis and selection for desired phenotype (such as the inability to metabolize benzoate or anthranilate) can be used to isolate bacterial strains in which target genes have been insertionally inactivated. See, e.g., K Nida & P P Cleary, Insertional inactivation of streptolysin S expression in *Streptococcus pyogenes*, J Bacteriol. 155(3):1156-61 (1983). Specific mutations or deletions in a particular gene can be constructed using cassette mutagenesis, for example, as described in J A Wells et al., Cassette mutagenesis: an efficient method for generation of multiple mutations at defined sites, Gene 34(2-3):315-23 (1985); whereby direct or random mutations are made in a selected portion of a gene, and then incorporated into the chromosomal copy of the gene by homologous recombination.

In one embodiment, both the organism from which the selection marker gene(s) is obtained and the host cell in which the selection marker gene(s) is utilized can be selected from a prokaryote. In a particular embodiment, both the organism from which the selection marker gene(s) is obtained and the host cell in which a selection marker gene(s) is utilized can be selected from a bacteria. In another embodiment, both the bacteria from which the selection marker gene(s) is obtained and the bacterial host cell in which a selection marker gene(s) is utilized, will be selected from the Proteobacteria. In still another embodiment, both the bacteria from which the selection marker gene(s) is obtained and the bacterial host cells in which a selection marker gene(s) is utilized, can be selected from the Pseudomonads and closely related bacteria or from a Subgroup thereof, as defined below.

In a particular embodiment, both the selection marker gene(s) source organism and the host cell can be selected from the same species. Preferably, the species will be a prokaryote; more preferably a bacterium, still more preferably a Proteobacterium. In another particular embodiment, both the selection marker gene(s) source organism and the host cell can be selected from the same species in a genus selected from the Pseudomonads and closely related bacteria or from a Subgroup thereof, as defined below. In one embodiment, both the selection marker gene(s) source organism and the host cell can be selected from a species of the genus *Pseudomonas*, particularly the species *Pseudomonas fluorescens*, and preferably the species *Pseudomonas fluorescens* biotype A.

Nucleic Acid Constructs

In still another aspect of the present invention, nucleic acid constructs are provided for use in the improved production of peptides. In one embodiment, a nucleic acid construct for use in transforming an auxotrophic host cell comprising a) a nucleic acid sequence encoding a recombinant polypeptide, and b) a nucleic acid sequence encoding a prototrophy-enabling enzyme is provided.

In one embodiment of the present invention, a nucleic acid construct is provided comprising nucleic acids that encode at least one biosynthetic enzyme capable of transforming an auxotrophic host cell to prototrophy. The biosynthetic enzyme can be any enzyme capable of allowing an auxotrophic host cell to survive on a selection medium that, without the expression of the biosynthetic enzyme, the host cell would be incapable of survival due to the auxotrophic metabolic deficiency. As such, the biosynthetic enzyme can be an enzyme that complements the metabolic deficiency of the auxotrophic host by restoring prototrophic ability to grow on non-auxotrophic metabolite supplemented media.

In an alternative embodiment, the present invention provides a nucleic acid construct that encodes at least one biosynthetic enzyme capable of transforming an auxotrophic host cell to prototrophy and an additional non-auxotrophic selection marker. Examples of non-auxotrophic selection markers are well known in the art, and can include markers that give rise to colorimetric/chromogenic or a luminescent reaction such as lacZ gene, the GUS gene, the CAT gene, the luxAB gene, antibiotic resistance selection markers such as amphotericin B, bacitracin, carbapenem, cephalosporin, ethambutol, fluoroquinolones, isonizid, cephalosporin, methicillin, oxacillin, vanomycin, streptomycin, quinolines, rifampin, rifampicin, sulfonamides, ampicillin, tetracycline, neomycin, cephalothin, erythromycin, streptomycin, kanamycin, gentamycin, penicillin, and chloramphenicol resistance genes, or other commonly used non-auxotrophic selection markers. In various embodiments, the expression system specifically lacks an antibiotic selection marker.

In another embodiment, the expression vector can comprise more than one biosynthetic enzyme capable of transforming an auxotrophic host cell to prototrophy. The biosynthetic enzymes can be any enzymes capable of allowing an auxotrophic host cell to survive on a selection medium that, without the expression of the biosynthetic enzyme, the host cell would be incapable of survival due to the auxotrophic metabolic deficiency. As such, the biosynthetic enzymes can be enzymes that complement the metabolic deficiencies of the auxotrophic host by restoring prototrophic ability to grow on non-auxotrophic metabolite supplemented media. For example, an expression vector comprises a first and second prototrophy-enabling selection marker gene, allowing the host cell containing the construct to be maintained under either or both of the conditions in which host cell survival requires the presence of the selection marker gene(s). When only one of the marker-gene dependent survival conditions is present, the corresponding marker gene must be expressed, and the other marker gene(s) may then be either active or inactive, though all necessary nutrients for which the cell remains auxotrophic will still be supplied by the medium. This permits the same target gene, or the same set of covalently linked target genes, encoding the desired transgenic product(s) and/or desired transgenic activity(ies), to be maintained in the host cell continuously as the host cell is transitioned between or among different conditions. The coding sequence of each of the chosen selection marker genes independently can be operably attached to either a constitutive or a regulated promoter.

Promoters

In a fermentation process, once expression of the target recombinant polypeptide is induced, it is ideal to have a high level of production in order to maximize efficiency of the expression system. The promoter initiates transcription and is generally positioned 10-100 nucleotides upstream of the ribosome binding site. Ideally, a promoter will be strong enough to allow for recombinant polypeptide accumulation of around 50% of the total cellular protein of the host cell, subject to tight regulation, and easily (and inexpensively) induced.

The promoters used in accordance with the present invention may be constitutive promoters or regulated promoters. Examples of commonly used inducible promoters and their subsequent inducers include lac (IPTG), lacUV5 (IPTG), tac (IPTG), trc (IPTG), P.sub.syn (IPTG), trp (tryptophan starvation), araBAD (1-arabinose), 1pp.sup.a (IPTG), 1pp-lac (IPTG), phoA (phosphate starvation), recA (nalidixic acid), proU (osmolarity), cst-1 (glucose starvation), teta (tretracylin), cada (pH), nar (anaerobic conditions), PL (thermal shift to 42.degree. C.), cspA (thermal shift to 200 C.), T7 (thermal induction), T7-lac operator (IPTG), T3-lac operator (IPTG), T5-lac operator (IPTG), T4 gene 32 (T4 infection), nprM-lac operator (IPTG), Pm (alkyl- or halo-benzoates), Pu (alkyl- or halo-toluenes), Psa1 (salicylates), and VHb (oxygen). See, for example, Makrides, S. C. (1996) Microbiol. Rev. 60, 512-538; Hannig G. & Makrides, S. C. (1998) TIBTECH 16, 54-60; Stevens, R. C. (2000) Structures 8, R177-R185. See, e.g.: J. Sanchez-Romero & V. De Lorenzo, Genetic Engineering of Nonpathogenic *Pseudomonas* strains as Biocatalysts for Industrial and Environmental Processes, in Manual of Industrial Microbiology and Biotechnology (A. Demain & J. Davies, eds.) pp. 460-74 (1999) (ASM Press, Washington, D.C.); H. Schweizer, Vectors to express foreign genes and techniques to monitor gene expression for Pseudomonads, Current-Opinion in Biotechnology, 12:439-445 (2001); and R. Slater & R. Williams, The Expression of Foreign DNA in Bacteria, in Molecular Biology and Biotechnology (J. Walker & R. Rapley, eds.) pp. 125-54 (2000) (The Royal Society of Chemistry, Cambridge, UK).

A promoter having the nucleotide sequence of a promoter native to the selected auxotrophic host cell can also be used to control expression of the transgene encoding the target polypeptide, e.g, a *Pseudomonas* anthranilate or benzoate operon promoter (Pant, Pben). Tandem promoters may also be used in which more than one promoter is covalently attached to another, whether the same or different in sequence, e.g., a Pant-Pben tandem promoter (interpromoter hybrid) or a Plac-Plac tandem promoter. See, for example, U.S. Patent Publication No. 20050202544, which is herein incorporated by reference in its entirety.

Regulated promoters utilize promoter regulatory proteins in order to control transcription of the gene of which the promoter is a part. Where a regulated promoter is used herein, a corresponding promoter regulatory protein will also be part of an expression system according to the present invention. Examples of promoter regulatory proteins include: activator proteins, e.g., *E. coli* catabolite activator protein, MalT protein; AraC family transcriptional activators; repressor proteins, e.g., *E. coli* LacI proteins; and dual-faction regulatory proteins, e.g., *E. coli* NagC protein. Many regulated-promoter/promoter-regulatory-protein pairs are known in the art.

Promoter regulatory proteins interact with an effector compound, i.e. a compound that reversibly or irreversibly associates with the regulatory protein so as to enable the protein to either release or bind to at least one DNA transcription regulatory region of the gene that is under the control of the promoter, thereby permitting or blocking the action of a transcriptase enzyme in initiating transcription of the gene. Effector compounds are classified as either inducers or co-repressors, and these compounds include native effector compounds and gratuitous inducer compounds. Many regulated-promoter/promoter-regulatory-protein/effector-compound trios are known in the art. Although an effector compound can be used throughout the cell culture or fermentation, in a particular embodiment in which a regulated promoter is used, after growth of a desired quantity or density of host cell biomass, an appropriate effector compound is added to the culture in order to directly or indirectly result in expression of the desired target gene(s).

By way of example, where a lac family promoter is utilized, a lacI gene, or derivative thereof such as a lacI.sup.Q or lacI.sup.Q1 gene, can also be present in the system. The lacI gene, which is (normally) a constitutively expressed gene, encodes the Lac repressor protein (LacI protein) which binds to the lac operator of these promoters. Thus, where a lac family promoter is utilized, the lacI gene can also be included and expressed in the expression system. In the case of the lac promoter family members, e.g., the tac promoter, the effector compound is an inducer, preferably a gratuitous inducer such as IPTG (isopropyl-.beta.-D-1-thiogalactopyranoside, also called "isopropylthiogalactoside").

In a particular embodiment, a lac or tac family promoter is utilized in the present invention, including Plac, Ptac, Ptrc, PtacII, PtacUV5, Ipp-PlacUV5, Ipp-lac, nprM-lac, T7lac, T5lac, T3lac, and Pmac.

Other Elements

Other regulatory elements can be included in an expression construct, including lacO sequences and derivatives, as discussed in U.S. Patent Publication No. 20050186666. Such elements include, but are not limited to, for example, transcriptional enhancer sequences, translational enhancer sequences, other promoters, activators, translational start and stop signals, transcription terminators, cistronic regulators, polycistronic regulators, tag sequences, such as nucleotide sequence "tags" and "tag" peptide coding sequences, which facilitates identification, separation, purification, or isolation of an expressed polypeptide, including His-tag, Flag-tag, T7-tag, S-tag, HSV-tag, B-tag, Strep-tag, polyarginine, polycysteine, polyphenylalanine, polyaspartic acid, (Ala-Trp-Trp-Pro)n, thioredoxin, beta-galactosidase, chloramphenicol acetyltransferase, cyclomaltodextrin gluconotransferase, CTP:CMP-3-deoxy-D-manno-octulosonate cytidyltransferase, trpE or trpLE, avidin, streptavidin, T7 gene 10, T4 gp55, Staphylococcal protein A, streptococcal protein G, GST, DHFR, CBP, MBP, galactose binding domain, Calmodulin binding domain, GFP, KSI, c-myc, ompT, ompA, pelB, NusA, ubiquitin, and hemosylin A.

At a minimum, a protein-encoding gene according to the present invention can include, in addition to the protein coding sequence, the following regulatory elements operably attached thereto: a promoter, a ribosome binding site (RBS), a transcription terminator, translational start and stop signals. Useful RBSs can be obtained from any of the species useful as host cells in expression systems according to the present invention, preferably from the selected host cell. Many specific and a variety of consensus RBSs are known, e.g., those described in and referenced by D. Frishman et al., Starts of bacterial genes: estimating the reliability of computer predictions, Gene 234(2):257-65 (8 Jul. 1999); and B. E. Suzek et al., A probabilistic method for identifying start codons in bacterial genomes, Bioinformatics 17(12): 1123-30 (December 2001). In addition, either native or synthetic RBSs may be used, e.g., those described in: EP 0207459 (synthetic RBSs); O. Ikehata et al., Primary structure of nitrile hydratase deduced from the nucleotide sequence of a *Rhodococcus* species and its expression in *Escherichia coli*, Eur. J. Biochem. 181(3):563-70 (1989) (native RBS sequence of AAGGAAG). Further examples of methods, vectors, and translation and transcription elements, and other elements useful in the present invention are described in, e.g.: U.S. Pat. No. 5,055,294 to Gilroy and U.S. Pat. No. 5,128,130 to Gilroy et al.; U.S. Pat. No. 5,281,532 to Rammler et al.; U.S. Pat. Nos. 4,695,455 and 4,861,595 to Barnes et al.; U.S. Pat. No. 4,755,465 to Gray et al.; and U.S. Pat. No. 5,169,760 to Wilcox.

Vectors

Transcription of the DNA encoding the enzymes of the present invention by a Pseudomonad host can further be increased by inserting an enhancer sequence into the vector or plasmid. Typical enhancers are cis-acting elements of DNA, usually about from 10 to 300 bp in size that act on the promoter to increase its transcription.

Generally, the recombinant expression vectors will include origins of replication and selectable markers permitting transformation of the Pseudomonad host cell, e.g., the prototrophy restoring genes of the present invention, and a promoter derived from a highly-expressed gene to direct transcription of a downstream structural sequence. Such promoters have been described above. The heterologous structural sequence is assembled in appropriate phase with translation initiation and termination sequences, and in certain embodiments, a leader sequence capable of directing secretion of the translated polypeptide. Optionally, and in accordance with the present invention, the heterologous sequence can encode a fusion polypeptide including an N-terminal identification peptide imparting desired characteristics, e.g., stabilization or simplified purification of expressed recombinant product.

Useful expression vectors for use in the present invention are constructed by inserting a structural DNA sequence encoding a desired target polypeptide together with suitable translation initiation and termination signals in operable reading phase with a functional promoter. The vector will comprise one or more phenotypic selectable markers and an origin of replication to ensure maintenance of the vector and to, if desirable, provide amplification within the host.

Vectors are known in the art as useful for expressing recombinant proteins in host cells, and any of these may be modified and used for expressing the genes according to the present invention. Such vectors include, e.g., plasmids, cosmids, and phage expression vectors. Examples of useful plasmid vectors that can be modified for use on the present invention include, but are not limited to, the expression plasmids pBBR1MCS, pDSK519, pKT240, pML122, pPS10, RK2, RK6, pRO1600, and RSF1010. Further examples can include pALTER-Ex1, pALTER-Ex2, pBAD/ His, pBAD/Myc-His, pBAD/gIII, pCal-n, pCal-n-EK, pCal-c, pCal-Kc, pcDNA 2.1, pDUAL, pET-3a-c, pET 9a-d, pET-11a-d, pET-12a-c, pET-14b, pET15b, pET-16b, pET-17b, pET-19b, pET-20b(+), pET-21a-d(+), pET-22b(+), pET-23a-d(+), pET24a-d(+), pET-25b(+), pET-26b(+), pET-27b (+), pET28a-c(+), pET-29a-c(+), pET-30a-c(+), pET31b(+), pET-32a-c(+), pET-33b(+), pET-34b(+), pET35b(+), pET-36b(+), pET-37b(+), pET-38b(+), pET-39b(+), pET-40b(+), pET411a-c(+), pET-42a-c(+pET43a-c(+), pETBlue-1, pET-Blue-2, pETBlue-3, pGEMEX-1, pGEMEX-2, pGEX1.lambda.T, pGEX-2T, pGEX-2TK, pGEX-3X, pGEX4T, pGEX-5X, pGEX-6P, pHAT10/11/12, pHAT20, pHAT-GFPuv, pKK223-3, pLEX, pMAL-c2X, pMAL-c2E, pMAL-c2g, pMAL-p2X, pMAL-p2E, pMAL-p2G, pProEX HT, pPROLar.A, pPROTet.E, pQE-9, pQE-16, pQE-30/31/32, pQE40, pQE-50, pQE-70, pQE-80/81/82L, pQE-100, pRSET, and pSE280, pSE380, pSE420, pThioHis, pTrc99A, pTrcHis, pTrcHis2, pTriEx-1, pTriEx-2, pTrxFus. Other examples of such useful vectors include those described by, e.g.: N. Hayase, in Appl. Envir. Microbiol. 60(9):3336-42 (September 1994); A. A. Lushnikov et al., in Basic Life Sci. 30:657-62 (1985); S. Graupner & W. Wackernagel, in Biomolec. Eng. 17(1):11-16. (October 2000); H. P. Schweizer, in Curr. Opin. Biotech. 12(5):439-45 (October 2001); M. Bagdasarian &. K. N. Timmis, in Curr. Topics Microbiol. Immunol. 96:47-67 (1982); T. Ishii et al., in FEMS Microbiol. Lett. 116(3):307-13 (Mar. 1, 1994); I. N. Olekhnovich & Y. K. Fomichev, in Gene 140(1):63-65 (Mar. 11, 1994); M. Tsuda & T. Nakazawa, in Gene 136(1-2):257-62 (Dec. 22, 1993); C. Nieto et al., in Gene 87(1):145-49 (Mar. 1, 1990); J. D. Jones & N. Gutterson, in Gene 61(3):299-306 (1987); M. Bagdasarian et al., in Gene 16(1-3):237-47 (December 1981); H. P. Schweizer et al., in Genet. Eng. (NY) 23:69-81 (2001); P. Mukhopadhyay et al., in J. Bact. 172(1):477-80 (January 1990); D. O. Wood et al., in J. Bact. 145(3):1448-51 (March 1981); Holtwick et al., in Microbiology 147(Pt 2):337-44 (Febuary 2001).

Further examples of expression vectors that can be useful in auxotrophic host cells include those listed in Table 1 as derived from the indicated replicons.

TABLE 1

Examples of Useful Expression Vectors

| Replicon | Vector(s) |
|---|---|
| PPS10 | PCN39, PCN51 |
| RSF1010 | PKT261-3 |
|  | PMMB66EH |
|  | PEB8 |
|  | PPLGN1 |
|  | PMYC1050 |
| RK2/RP1 | PRK415 |
|  | PJB653 |
| PRO1600 | PUCP |
|  | PBSP |

The expression plasmid, RSF1010, is described, e.g., by F. Heffron et al., in Proc. Nat'l Acad. Sci. USA 72(9):3623-27 (September 1975), and by K. Nagahari & K. Sakaguchi, in J. Bact. 133(3):1527-29 (March 1978). Plasmid RSF10100 and derivatives thereof are particularly useful vectors in the present invention. Exemplary, useful derivatives of RSF1010, which are known in the art, include, e.g., pKT212, pKT214, pKT231 and related plasmids, and pMYC1050 and related plasmids (see, e.g., U.S. Pat. Nos. 5,527,883 and 5,840,554 to Thompson et al.), such as, e.g., pMYC1803. Plasmid pMYC1803 is derived from the RSF1010-based plasmid pTJS260 (see U.S. Pat. No. 5,169,760 to Wilcox), which carries a regulated tetracycline resistance marker and the replication and mobilization loci from the RSF1010 plasmid. Other exemplary useful vectors include those described in U.S. Pat. No. 4,680,264 to Puhler et al.

In one embodiment, an expression plasmid is used as the expression vector. In another embodiment, RSF1010 or a derivative thereof is used as the expression vector. In still another embodiment, pMYC1050 or a derivative thereof, or pMYC1803 or a derivative thereof, is used as the expression vector.

Host Cell

In this embodiment, the host cell can be selected from "Gram-negative Proteobacteria Subgroup 18." "Gram-negative Proteobacteria Subgroup 18" is defined as the group of all subspecies, varieties, strains, and other sub-special units of the species *Pseudomonas fluorescens*, including those belonging, e.g., to the following (with the ATCC or other deposit numbers of exemplary strain(s) shown in parenthesis): *Pseudomonas fluorescens* biotype A, also called biovar 1 or biovar I (ATCC 13525); *Pseudomonas fluorescens* biotype B, also called biovar 2 or biovar II (ATCC 17816); *Pseudomonas fluorescens* biotype C, also called biovar 3 or biovar III (ATCC 17400); *Pseudomonas fluorescens* biotype F, also called biovar 4 or biovar IV (ATCC 12983); *Pseudomonas fluorescens* biotype G, also called biovar 5 or biovar V (ATCC 17518); *Pseudomonas fluorescens* biovar VI; *Pseudomonas fluorescens* Pf0-1; *Pseudomonas fluorescens* Pf-5 (ATCC BAA-477); *Pseudomonas fluorescens* SBW25; and *Pseudomonas fluorescens* subsp. *cellulosa* (NCIMB 10462).

The host cell can be selected from "Gram-negative Proteobacteria Subgroup 19." "Gram-negative Proteobacteria Subgroup 19" is defined as the group of all strains of *Pseudomonas fluorescens* biotype A. It has been discovered that *Pseudomonas fluorescens* (Pf) does not exhibit the inherent problems associated with cross-feeding observed in other host cell systems, for example, *E. coli* and yeast. While not wanting to be bound by any particular theory, it is thought that auxotrophic *Pseudomonas fluorescens* is a particularly suitable organism for use as a host cell because of the observed inability of a Pf auxotrophic cell to out compete an auxotrophic cell containing a prototrophic-enabling plasmid on a supplemented medium that contains the auxotrophic metabolite, indicating an innate difficulty of an Pf auxotroph to import the required metabolite. Therefore, Pf auxotrophic cells that lose the selection marker plasmid do not gain a selective advantage over Pf auxotrophic cells containing the selection marker, even in the presence of a supplemental metabolite, greatly reducing any potential effects of cross-feeding. Because of the reduced effects of cross-feeding, production yields of the recombinant polypeptide in a fermentation run (particularly large-batch fermentation runs) are not reduced due to the presence of non-recombinant polypeptide producing cells.

A particularly preferred strain of this biotype is *P. fluorescens* strain MB101 (see U.S. Pat. No. 5,169,760 to Wilcox), and derivatives thereof. An example of a preferred derivative thereof is *P. fluorescens* strain MB214, constructed by inserting into the MB101 chromosomal asd (aspartate dehydrogenase gene) locus, a native *E. coli* PlacI-lacI-lacZYA construct (i.e. in which PlacZ was deleted).

Additional *P. fluorescens* strains that can be used in the present invention include *Pseudomonas fluorescens* Migula and *Pseudomonas fluorescens* Loitokitok, having the following ATCC designations: [NCIB 8286]; NRRL B-1244; NCIB 8865 strain CO1; NCIB 8866 strain CO2; 1291 [ATCC 17458; IFO 15837; NCIB 8917; LA; NRRL B-1864; pyrrolidine; PW2 [ICMP 3966; NCPPB 967; NRRL B-899]; 13475; NCTC 10038; NRRL B-1603 [6; IFO 15840]; 52-1C; CCEB 488-A [BU 140]; CCEB 553 [EM 15/47]; IAM 1008 [AHH-27]; IAM 1055 [AHH-23]; 1 [IFO 15842]; 12 [ATCC 25323; NIH 11; den Dooren de Jong 216]; 18 [IFO 15833; WRRL P-7]; 93 [TR-10]; 108 [52-22; IFO 15832]; 143 [IFO 15836; PL]; 149 [2-40-40; IFO 15838]; 182 [IFO 3081; PJ 73]; 184 [IFO 15830]; 185 [W2 L-1]; 186 [IFO 15829; PJ 79]; 187 [NCPPB 263]; 188 [NCPPB 316]; 189 [PJ227; 1208]; 191 [IFO 15834; PJ 236; 22/1]; 194 [Klinge R-60; PJ 253]; 196 [PJ 288]; 197 [PJ 290]; 198 [PJ 302]; 201 [PJ 368]; 202 [PJ 372]; 203 [PJ 376]; 204 [IFO 15835; PJ 682]; 205 [PJ 686]; 206 [PJ 692]; 207 [PJ 693]; 208 [PJ 722]; 212. [PJ 832]; 215 [PJ 849]; 216 [PJ 885]; 267 [B-9]; 271 [B-1612]; 401 [C71A; IFO 15831; PJ 187]; NRRL B-3178 [4; IFO. 15841]; KY 8521; 3081; 30-21; [IFO 3081]; N; PYR; PW; D946-B83 [BU 2183; FERM-P 3328]; P-2563 [FERM-P 2894; IFO 13658]; IAM-1126 [43F]; M-1; A506 [A5-06]; A505 [A5-05-1]; A526 [A5-26]; B69; 72; NRRL B-4290; PMW6 [NCIB 11615]; SC 12936; A1 [IFO 15839]; F 1847 [CDC-EB]; F 1848 [CDC 93]; NCIB 10586; P17; F-12; AmMS 257; PRA25; 6133D02; 6519E01; Ni; SC15208; BNL-WVC; NCTC 2583 [NCIB 8194]; H13; 1013 [ATCC 11251; CCEB 295]; IFO 3903; 1062; or Pf-5.

In other embodiments, the host cell can be any cell capable of producing a protein or polypeptide of interest, including a *P. fluorescens* cell as described above. The most commonly used systems to produce proteins or polypeptides of interest include certain bacterial cells, particularly *E. coli*, because of their relatively inexpensive growth requirements and potential capacity to produce protein in large batch cultures. Yeasts are also used to express biologically relevant proteins and polypeptides, particularly for research purposes. Systems include *Saccharomyces cerevisiae* or *Pichia pastoris*. These systems are well characterized, provide generally acceptable levels of total protein expression and are comparatively fast and inexpensive. Insect cell expression systems have also emerged as an alternative for expressing recombinant proteins in biologically active form. In some cases, correctly folded proteins that are post-translationally modified can be produced. Mammalian cell expression systems, such as Chinese hamster ovary cells, have also been used for the expression of proteins or polypeptides of interest. On a small scale, these expression systems are often effective. Certain biologics can be derived from proteins, particularly in animal or human health applications. In another embodiment, the host cell is a plant cell, including, but not limited to, a tobacco cell, corn, a cell from an *Arabidopsis* species, potato or rice cell. In another embodiment, a multicellular organism is analyzed or is modified in the process, including but not limited to a transgenic organism. Techniques for analyzing and/or modifying a multicellular organism are generally based on techniques described for modifying cells described below.

In another embodiment, the host cell can be a prokaryote such as a bacterial cell including, but not limited to an *Escherichia* or a *Pseudomonas* species. Typical bacterial cells are described, for example, in "Biological Diversity: Bacteria and Archaeans", a chapter of the On-Line Biology Book, provided by Dr M J Farabee of the Estrella Mountain Community College, Arizona, USA at the website www.emc.maricotpa.edu/faculty/farabee/BIOBK/BioBookDiversity. In certain embodiments, the host cell can be a Pseudomonad cell, and can typically be a *P. fluorescens* cell. In other embodiments, the host cell can also be an *E. coli* cell. In another embodiment the host cell can be a eukaryotic cell, for example an insect cell, including but not limited to a cell from a *Spodoptera, Trichoplusia, Drosophila* or an *Estigmene* species, or a mammalian cell, including but not limited to a murine cell, a hamster cell, a monkey, a primate or a human cell.

In one embodiment, the host cell can be a member of any of the bacterial taxa. The cell can, for example, be a member of any species of eubacteria. The host can be a member of any one of the taxa: *Acidobacteria, Actinobacteira, Aquificae, Bacteroidetes, Chlorobi, Chlamydiae, Choroflexi, Chrysiogenetes, Cyanobacteria, Deferribacteres, Deinococcus, Dictyoglomi, Fibrobacteres, Firmicutes, Fusobacteria, Gemmatimonadetes, Lentisphaerae, Nitrospirae, Planctomycetes, Proteobacteria, Spirochaetes, Thermodesulfobacteria, Thermomicrobia, Thermotogae, Thermus (Thermales),* or *Verrucomicrobia.* In a embodiment of a eubacterial host cell, the cell can be a member of any species of eubacteria, excluding *Cyanobacteria.*

The bacterial host can also be a member of any species of Proteobacteria. A proteobacterial host cell can be a member of any one of the taxa *Alphaproteobacteria, Betaproteobacteria, Gammaproteobacteria, Deltaproteobacteria,* or *Epsilonproteobacteria.* In addition, the host can be a member of any one of the taxa *Alphaproteobacteria, Betaproteobacteria,* or *Gammaproteobacteria,* and a member of any species of Gammaproteobacteria.

In one embodiment of a Gamma Proteobacterial host, the host will be member of any one of the taxa *Aeromonadales, Alteromonadales, Enterobacteriales, Pseudomonadales,* or *Xanthomonadales*; or a member of any species of the *Enterobacteriales* or *Pseudomonadales.* In one embodiment, the host cell can be of the order *Enterobacteriales*, the host cell will be a member of the family Enterobacteriaceae, or may be a member of any one of the genera *Erwinia, Escherichia,* or *Serratia*; or a member of the genus *Escherichia.* Where the host cell is of the order *Pseudomonadales,* the host cell may be a member of the family Pseudomonadaceae, including the genus *Pseudomonas.* Gamma Proteobacterial hosts include members of the species *Escherichia coli* and members of the species *Pseudomonas fluorescens.*

Other *Pseudomonas* organisms may also be useful. Pseudomonads and closely related species include Gram-negative Proteobacteria Subgroup 1, which include the group of Proteobacteria belonging to the families and/or genera described as "Gram-Negative Aerobic Rods and Cocci" by R. E. Buchanan and N. E. Gibbons (eds.), Bergey's Manual of Determinative Bacteriology, pp. 217-289 (8th ed., 1974) (The Williams & Wilkins Co., Baltimore, Md., USA) (hereinafter "Bergey (1974)"). Table 2 presents these families and genera of organisms.

TABLE 2

Families and Genera Listed in the Part, "Gram-Negative Aerobic Rods and Cocci" (in Bergey (1974))

| | |
|---|---|
| Family I. | *Gluconobacter* |
| Pseudomomonaceae | *Pseudomonas* |
| | *Xanthomonas* |
| | *Zoogloea* |
| Family II. | *Azomonas* |
| Azotobacteraceae | *Azotobacter* |
| | *Beijerinckia* |
| | *Derxia* |

TABLE 2-continued

Families and Genera Listed in the Part, "Gram-Negative Aerobic Rods and Cocci" (in Bergey (1974))

| | |
|---|---|
| Family III. | *Agrobacterium* |
| Rhizobiaceae | *Rhizobium* |
| Family IV. | *Methylococcus* |
| Methylomonadaceae | *Methylomonas* |
| Family V. | *Halobacterium* |
| Halobacteriaceae | *Halococcus* |
| Other Genera | *Acetobacter* |
| | *Alcaligenes* |
| | *Bordetella* |
| | *Brucella* |
| | *Francisella* |
| | *Thermus* |

"Gram-negative Proteobacteria Subgroup 1" also includes Proteobacteria that would be classified in this heading according to the criteria used in the classification. The heading also includes groups that were previously classified in this section but are no longer, such as the genera *Acidovorax, Brevundimonas, Burkholderia, Hydrogenophaga, Oceanimonas, Ralstonia,* and *Stenotrophomonas,* the genus *Sphingomonas* (and the genus *Blastomonas*, derived therefrom), which was created by regrouping organisms belonging to (and previously called species of) the genus *Xanthomonas,* the genus *Acidomonas*, which was created by regrouping organisms belonging to the genus *Acetobacter* as defined in Bergey (1974). In addition hosts can include cells from the genus *Pseudomonas, Pseudomonas enalia* (ATCC 14393), *Pseudomonas nigrifaciensi* (ATCC 19375), and *Pseudomonas putrefaciens* (ATCC 8071), which have been reclassified respectively as *Alteromonas haloplanktis, Alteromonas nigrifaciens,* and *Alteromonas putrefaciens.* Similarly, e.g., *Pseudomonas acidovorans* (ATCC 15668) and *Pseudomonas testosteroni* (ATCC 11996) have since been reclassified as *Comamonas acidovorans* and *Comamonas testosteroni,* respectively; and *Pseudomonas nigrifaciens* (ATCC 19375) and *Pseudomonas piscicida* (ATCC 15057) have been reclassified respectively as *Pseudoalteromonas nigrifaciens* and *Pseudoalteromonas piscicida.* "Gram-negative Proteobacteria Subgroup 1" also includes Proteobacteria classified as belonging to any of the families. Pseudomonadaceae, Azotobacteraceae (now often called by the synonym, the "*Azotobacter* group" of Pseudomonadaceae), Rhizobiaceae, and Methylomonadaceae (now often called by the synonym, "Methylococcaceae"). Consequently, in addition to those genera otherwise described herein, further Proteobacterial genera falling within "Gram-negative Proteobacteria Subgroup 1" include: 1) *Azotobacter* group bacteria of the genus *Azorhizophilus;* 2) Pseudomonadaceae family bacteria of the genera *Cellvibrio, Oligella,* and *Teredinibacter;* 3) Rhizobiaceae family bacteria of the genera *Chelatobacter, Ensifer, Liberibacter* (also called "*Candidatus Liberibacter*"), and *Sinorhizobium*; and 4) Methylococcaceae family bacteria of the genera *Methylobacter, Methylocaldum, Methylomicrobium, Methylosarcina,* and *Methylosphaera.*

In another embodiment, the host cell is selected from "Gram-negative Proteobacteria Subgroup 2." "Gram-negative Proteobacteria Subgroup 2" is defined as the group of Proteobacteria of the following genera (with the total numbers of catalog-listed, publicly-available, deposited strains thereof indicated in parenthesis, all deposited at ATCC, except as otherwise indicated): *Acidomonas* (2); *Acetobacter* (93); *Gluconobacter* (37); *Brevundimonas* (23); *Beyerinckia* (13); *Derxia* (2); *Brucella* (4); *Agrobacterium* (79); *Chelatobacter* (2); *Ensifer* (3); *Rhizobium* (144); *Sinorhizo-*

*bium* (24); *Blastomonas* (1); *Sphingomonas* (27); *Alcaligenes* (88); *Bordetella* (43); *Burkholderia* (73); *Ralstonia* (33); *Acidovorax* (20); *Hydrogenophaga* (9); *Zoogloea* (9); *Methylobacter* (2); *Methylocaldum* (1 at NCIMB); *Methylococcus* (2); *Methylomicrobium* (2); *Methylomonas* (9); *Methylosarcina* (1); *Methylosphaera*; *Azomonas* (9); *Azorhizophilus* (5); *Azotobacter* (64); *Cellvibrio* (3); *Oligella* (5); *Pseudomonas* (1139); *Francisella* (4); *Xanthomonas* (229); *Stenotrophomonas* (50); and *Oceanimonas* (4).

Exemplary host cell species of "Gram-negative Proteobacteria Subgroup 2" include, but are not limited to the following bacteria (with the ATCC or other deposit numbers of exemplary strain(s) thereof shown in parenthesis): *Acidomonas methanolica* (ATCC 43581); *Acetobacter aceti* (ATCC 15973); *Gluconobacter oxydans* (ATCC 19357); *Brevundimonas diminuta* (ATCC 11568); *Beijerinckia indica* (ATCC 9039 and ATCC 19361); *Derxia gummosa* (ATCC 15994); *Brucella melitensis* (ATCC 23456), *Brucella abortus* (ATCC 23448); *Agrobacterium tumefaciens* (ATCC 23308), *Agrobacterium radiobacter* (ATCC 19358), *Agrobacterium rhizogenes* (ATCC 11325); *Chelatobacter heintzii* (ATCC 29600); *Ensifer adhaerens* (ATCC 33212); *Rhizobium leguminosarum* (ATCC 10004); *Sinorhizobium fredii* (ATCC 35423); *Blastomonas natatoria* (ATCC 35951); *Sphingomonas paucimobilis* (ATCC 29837); *Alcaligenes faecalis* (ATCC 8750); *Bordetella pertussis* (ATCC 9797); *Burkholderia cepacia* (ATCC 25416); *Ralstonia pickettii* (ATCC 27511); *Acidovorax facilis* (ATCC 11228); *Hydrogenophagaflava* (ATCC 33667); *Zoogloea ramigera* (ATCC 19544); *Methylobacter luteus* (ATCC 49878); *Methylocaldum gracile* (NCIMB 11912); *Methylococcus capsulatus* (ATCC 19069); *Methylomicrobium agile* (ATCC 35068); *Methylomonas methanica* (ATCC 35067); *Methylosarcina fibrata* (ATCC 700909); *Methylosphaera hansonii* (ACAM 549); *Azomonas agilis* (ATCC 7494); *Azorhizophilus paspali* (ATCC 23833); *Azotobacter chroococcum* (ATCC 9043); *Cellvibrio mixtus* (UQM 2601); *Oligella urethralis* (ATCC 17960); *Pseudomonas aeruginosa* (ATCC 10145), *Pseudomonas fluorescens* (ATCC 35858); *Francisella tularensis* (ATCC 6223); *Stenotrophomonas maltophilia* (ATCC 13637); *Xanthomonas campestris* (ATCC 33913); and *Oceanimonas doudoroffii* (ATCC 27123).

In another embodiment, the host cell is selected from "Gram-negative Proteobacteria Subgroup 3." "Gram-negative Proteobacteria Subgroup 3" is defined as the group of Proteobacteria of the following genera: *Brevundimonas; Agrobacterium; Rhizobium; Sinorhizobium; Blastomonas; Sphingomonas; Alcaligenes; Burkholderia; Ralstonia; Acidovorax; Hydrogenophaga; Methylobacter; Methylocaldum; Methylococcus; Methylomicrobium; Methylomonas; Methylosarcina; Methylosphaera; Azomonas; Azorhizophilus; Azotobacter; Cellvibrio; Oligella; Pseudomonas; Teredinibacter; Francisella; Stenotrophomonas; Xanthomonas*; and *Oceanimonas*.

In another embodiment, the host cell is selected from "Gram-negative Proteobacteria Subgroup 4." "Gram-negative Proteobacteria Subgroup 4" is defined as the group of Proteobacteria of the following genera: *Brevundimonas; Blastomonas; Sphingomonas; Burkholderia; Ralstonia; Acidovorax; Hydrogenophaga; Methylobacter; Methylocaldum; Methylococcus; Methylomicrobium; Methylomonas; Methylosarcina; Methylosphaera; Azomonas; Azorhizophilus; Azotobacter; Cellvibrio; Oligella; Pseudomonas; Teredinibacter; Francisella; Stenotrophomonas; Xanthomonas*; and *Oceanimonas*.

In another embodiment, the host cell is selected from "Gram-negative Proteobacteria Subgroup 5." "Gram-negative Proteobacteria Subgroup 5" is defined as the group of Proteobacteria of the following genera: *Methylobacter; Methylocaldum; Methylococcus; Methylomicrobium; Methylomonas; Methylosarcina; Methylosphaera; Azomonas; Azorhizophilus; Azotobacter; Cellvibrio; Oligella; Pseudomonas; Teredinibacter; Francisella; Stenotrophomonas; Xanthomonas*; and *Oceanimonas*.

The host cell can be selected from "Gram-negative Proteobacteria Subgroup 6." "Gram-negative Proteobacteria Subgroup 6" is defined as the group of Proteobacteria of the following genera: *Brevundimonas; Blastomonas; Sphingomonas; Burkholderia; Ralstonia; Acidovorax; Hydrogenophaga; Azomonas; Azorhizophilus; Azotobacter; Cellvibrio; Oligella; Pseudomonas; Teredinibacter; Stenotrophomonas; Xanthomonas*; and *Oceanimonas*.

The host cell can be selected from "Gram-negative Proteobacteria Subgroup 7." "Gram-negative Proteobacteria Subgroup 7" is defined as the group of Proteobacteria of the following genera: *Azomonas; Azorhizophilus; Azotobacter; Cellvibrio; Oligella; Pseudomonas; Teredinibacter; Stenotrophomonas; Xanthomonas*; and *Oceanimonas*.

The host cell can be selected from "Gram-negative Proteobacteria Subgroup 8." "Gram-negative Proteobacteria Subgroup 8" is defined as the group of Proteobacteria of the following genera: *Brevundimonas; Blastomonas; Sphingomonas; Burkholderia; Ralstonia; Acidovorax; Hydrogenophaga; Pseudomonas; Stenotrophomonas; Xanthomonas*; and *Oceanimonas*.

The host cell can be selected from "Gram-negative Proteobacteria Subgroup 9." "Gram-negative Proteobacteria Subgroup 9" is defined as the group of Proteobacteria of the following genera: *Brevundimonas; Burkholderia; Ralstonia; Acidovorax; Hydrogenophaga; Pseudomonas; Stenotrophomonas*; and *Oceanimonas*.

The host cell can be selected from "Gram-negative Proteobacteria Subgroup 10." "Gram-negative Proteobacteria Subgroup 10" is defined as the group of Proteobacteria of the following genera: *Burkholderia; Ralstonia; Pseudomonas; Stenotrophomonas*; and *Xanthomonas*.

The host cell can be selected from "Gram-negative Proteobacteria Subgroup 11." "Gram-negative Proteobacteria Subgroup 11" is defined as the group of Proteobacteria of the genera: *Pseudomonas; Stenotrophomonas*; and *Xanthomonas*. The host cell can be selected from "Gram-negative Proteobacteria Subgroup 12." "Gram-negative Proteobacteria Subgroup 12" is defined as the group of Proteobacteria of the following genera: *Burkholderia; Ralstonia; Pseudomonas*. The host cell can be selected from "Gram-negative Proteobacteria Subgroup 13." "Gram-negative Proteobacteria Subgroup 13" is defined as the group of Proteobacteria of the following genera: *Burkholderia; Ralstonia; Pseudomonas*; and *Xanthomonas*. The host cell can be selected from "Gram-negative Proteobacteria Subgroup 14." "Gram-negative Proteobacteria Subgroup 14" is defined as the group of Proteobacteria of the following genera: *Pseudomonas* and *Xanthomonas*. The host cell can be selected from "Gram-negative Proteobacteria Subgroup 15." "Gram-negative Proteobacteria Subgroup 15" is defined as the group of Proteobacteria of the genus *Pseudomonas*.

The host cell can be selected from "Gram-negative Proteobacteria Subgroup 16." "Gram-negative Proteobacteria Subgroup 16" is defined as the group of Proteobacteria of the following *Pseudomonas* species (with the ATCC or other deposit numbers of exemplary strain(s) shown in parenthesis): *Pseudomonas abietaniphila* (ATCC 700689); *Pseudomonas aeruginosa* (ATCC 10145); *Pseudomonas alcaligenes* (ATCC 14909); *Pseudomonas anguilliseptica*

(ATCC 33660); *Pseudomonas citronellolis* (ATCC 13674); *Pseudomonas flavescens* (ATCC 51555); *Pseudomonas mendocina* (ATCC 25411); *Pseudomonas nitroreducens* (ATCC 33634); *Pseudomonas oleovorans* (ATCC 8062); *Pseudomonas pseudoalcaligenes* (ATCC 17440); *Pseudomonas resinovorans* (ATCC 14235); *Pseudomonas straminea* (ATCC 33636); *Pseudomonas agarici* (ATCC 25941); *Pseudomonas alcaliphila; Pseudomonas alginovora; Pseudomonas andersonii; Pseudomonas asplenii* (ATCC 23835); *Pseudomonas azelaica* (ATCC 27162); *Pseudomonas beyerinckii* (ATCC 19372); *Pseudomonas borealis; Pseudomonas boreopolis* (ATCC 33662); *Pseudomonas brassicacearum; Pseudomonas butanovora* (ATCC 43655); *Pseudomonas cellulosa* (ATCC 55703); *Pseudomonas aurantiaca* (ATCC 33663); *Pseudomonas chlororaphis* (ATCC 9446, ATCC 13985, ATCC 17418, ATCC 17461); *Pseudomonas fragi* (ATCC 4973); *Pseudomonas lundensis* (ATCC 49968); *Pseudomonas taetrolens* (ATCC 4683); *Pseudomonas cissicola* (ATCC 33616); *Pseudomonas coronafaciens; Pseudomonas diterpeniphila; Pseudomonas elongata* (ATCC 10144); *Pseudomonasflectens* (ATCC 12775); *Pseudomonas azotoformans; Pseudomonas brenneri; Pseudomonas cedrella; Pseudomonas corrugata* (ATCC 29736); *Pseudomonas extremorientalis; Pseudomonas fluorescens* (ATCC 35858); *Pseudomonas gessardii; Pseudomonas libanensis; Pseudomonas mandelii* (ATCC 700871); *Pseudomonas marginalis* (ATCC 10844); *Pseudomonas migulae; Pseudomonas mucidolens* (ATCC 4685); *Pseudomonas orientalis; Pseudomonas rhodesiae; Pseudomonas synxantha* (ATCC 9890); *Pseudomonas tolaasii* (ATCC 33618); *Pseudomonas veronii* (ATCC 700474); *Pseudomonas frederiksbergensis; Pseudomonas geniculata* (ATCC 19374); *Pseudomonas gingeri; Pseudomonas graminis; Pseudomonas grimontii; Pseudomonas halodenitrificans; Pseudomonas halophila; Pseudomonas hibiscicola* (ATCC 19867); *Pseudomonas huttiensis* (ATCC 14670); *Pseudomonas hydrogenovora; Pseudomonas jessenii* (ATCC 700870); *Pseudomonas kilonensis; Pseudomonas lanceolata* (ATCC 14669); *Pseudomonas lini; Pseudomonas marginata* (ATCC 25417); *Pseudomonas mephitica* (ATCC 33665); *Pseudomonas denitrificans* (ATCC 19244); *Pseudomonas pertucinogena* (ATCC 190); *Pseudomonas pictorum* (ATCC 23328); *Pseudomonas psychrophila; Pseudomonas filva* (ATCC 31418); *Pseudomonas monteilii* (ATCC 700476); *Pseudomonas mosselii; Pseudomonas oryzihabitans* (ATCC 43272); *Pseudomonas plecoglossicida* (ATCC 700383); *Pseudomonas putida* (ATCC 12633); *Pseudomonas reactans; Pseudomonas spinosa* (ATCC 14606); *Pseudomonas balearica; Pseudomonas luteola* (ATCC 43273); *Pseudomonas stutzeri* (ATCC 17588); *Pseudomonas amygdali* (ATCC 33614); *Pseudomonas avellanae* (ATCC 700331); *Pseudomonas caricapapayae* (ATCC 33615); *Pseudomonas cichorii* (ATCC 10857); *Pseudomonas ficuserectae* (ATCC 35104); *Pseudomonas fuscovaginae; Pseudomonas meliae* (ATCC 33050); *Pseudomonas syringae* (ATCC 19310); *Pseudomonas viridiflava* (ATCC 13223); *Pseudomonas thermocarboxydovorans* (ATCC 35961); *Pseudomonas thermotolerans; Pseudomonas thivervalensis; Pseudomonas vancouverensis* (ATCC 700688); *Pseudomonas wisconsinensis*; and *Pseudomonas xiamenensis*.

The host cell can be selected from "Gram-negative Proteobacteria Subgroup 17." "Gram-negative Proteobacteria Subgroup 17" is defined as the group of Proteobacteria known in the art as the "fluorescent Pseudomonads" including those belonging, e.g., to the following *Pseudomonas* species: *Pseudomonas azotoformans; Pseudomonas brenneri; Pseudomonas cedrella; Pseudomonas corrugata; Pseudomonas extremorientalis; Pseudomonas fluorescens; Pseudomonas gessardii; Pseudomonas libanensis; Pseudomonas mandelii; Pseudomonas marginalis; Pseudomonas migulae; Pseudomonas mucidolens; Pseudomonas orientalis; Pseudomonas rhodesiae; Pseudomonas synxantha; Pseudomonas tolaasii*; and *Pseudomonas veronii*.

Other suitable hosts include those classified in other parts of the reference, such as Gram (+) Proteobacteria. In one embodiment, the host cell is an *E. coli*. The genome sequence for *E. coli* has been established for *E. coli* MG1655 (Blattner, et al. (1997) The complete genome sequence of *Escherichia coli* K-12, Science 277(5331): 1453-74) and DNA microarrays are available commercially for *E. coli* K12 (MWG Inc, High Point, N.C.). *E. coli* can be cultured in either a rich medium such as Luria-Bertani (LB) (10 g/L tryptone, 5 g/L NaCl, 5 g/L yeast extract) or a defined minimal medium such as M9 (6 g/L Na2HPO4, 3 g/L KH2PO4, 1 g/L NH4Cl, 0.5 g/L NaCl, pH 7.4) with an appropriate carbon source such as 1% glucose. Routinely, an over night culture of *E. coli* cells is diluted and inoculated into fresh rich or minimal medium in either a shake flask or a fermentor and grown at 37° C.

A host can also be of mammalian origin, such as a cell derived from a mammal including any human or non-human mammal. Mammals can include, but are not limited to primates, monkeys, porcine, ovine, bovine, rodents, ungulates, pigs, swine, sheep, lambs, goats, cattle, deer, mules, horses, monkeys, apes, dogs, cats, rats, and mice.

lambs, goats, cattle, deer, mules, horses, monkeys, apes, dogs, cats, rats, and mice.

A host cell may also be of plant origin. Any plant can be selected for the identification of genes and regulatory sequences. Examples of suitable plant targets for the isolation of genes and regulatory sequences would include but are not limited to alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassaya, castorbean, cauliflower, celery, cherry, chicory, cilantro, citrus, clementines, clover, coconut, coffee, corn, cotton, cranberry, cucumber, Douglas fir, eggplant, endive, escarole, *eucalyptus*, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, an ornamental plant, palm, *papaya*, parsley, parsnip, pea, peach, peanut, pear, pepper, persimmon, pine, pineapple, plantain, plum, pomegranate, poplar, potato, pumpkin, quince, *radiata* pine, radiscchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini. In some embodiments, plants useful in the method are *Arabidopsis*, corn, wheat, soybean, and cotton.

Expression of Recombinant Polypeptides in an Auxotrophic Host Cell

In one aspect of the present invention, processes of expressing recombinant polypeptides for use in improved protein production are provided. In accordance with one aspect of the present invention, there is provided a method for producing a recombinant polypeptide of interest. The process includes obtaining a population of cells auxotrophic for a first metabolite and a second metabolite. In one embodiment, the second metabolite is a natural amino acid.

In addition, the method includes contacting the population of cells with a first nucleic acid construct comprising an auxotrophic selection marker, wherein the auxotrophic selection marker comprises a first nucleic acid sequence encoding at least one polypeptide active in the biosynthesis of the first metabolite, and wherein expression of the auxotrophic selection marker restores prototrophy for the first metabolite. The population of cells is contacted with a second nucleic acid construct comprising a second nucleic acid sequence encoding the recombinant polypeptide of interest; and a promoter operably attached to the second nucleic acid sequence so as to direct expression of the second nucleic acid sequence. The population of cells is subjected to a first medium lacking the first metabolite under conditions such that transfected cells having restored prototrophy for the first metabolite are obtained. The transfected cells are subjected to a second medium comprising a non-natural amino acid correlating to the second metabolite under conditions such that the second nucleic acid sequence is expressed to produce the recombinant polypeptide of interest having the non-natural amino acid incorporated therein. In the method, the first medium and the second medium may be the same or different. In other words, the first medium may contain the non-natural amino acid, and in such case, may serve as the second medium. Alternatively, the first medium lacks the non-natural amino acid. Once the transfected cells are obtained, then these cells are subjected to a second medium containing a non-natural amino acid.

In accordance with another aspect of the present invention, there is provided a method for producing a recombinant polypeptide of interest. The method generally comprises: introducing into a host cell that is auxotrophic for a first metabolite a first nucleic acid construct comprising an auxotrophic selection marker. The auxotrophic selection marker comprises a first nucleic acid sequence encoding at least one polypeptide active in the biosynthesis of the first metabolite, and expression of the auxotrophic selection marker restores prototrophy for the first metabolite to the auxotrophic host cell. The method further includes introducing into the host cell: (i) a second nucleic acid construct comprising a second nucleic acid sequence encoding the recombinant polypeptide of interest; (ii) a third nucleic acid sequence encoding an orthogonal tRNA synthetase, (iii) a fourth nucleic acid sequence encoding an orthogonal tRNA; and (iv) a promoter operably attached to the second, third and/or fourth nucleic acid sequences so as to direct expression of the second nucleic acid, third and/or fourth nucleic acid sequences in the auxotrophic host cell. The auxotrophic host cell is subjected to a medium that lacks the first metabolite to select for transfected cells. The medium may comprise or be supplanted with a second medium that comprises a non-natural amino acid under conditions whereby expressed orthogonal tRNA interactable with the expressed orthogonal tRNA synthetase facilitates incorporation of the non-natural amino acid into the recombinant polypeptide of interest during translation.

In accordance with yet another aspect of the present invention, there is provided a method for producing a recombinant polypeptide of interest. The method embodiment generally comprises a) introducing into a host cell that is auxotrophic for a first metabolite required for survival of the host cell: (i) a first nucleic acid construct comprising an auxotrophic selection marker, wherein the auxotrophic selection marker comprises a first nucleic acid sequence encoding at least one polypeptide active in the biosynthesis of the first metabolite, and wherein expression of the auxotrophic selection marker restores prototrophy for the first metabolite to the auxotrophic host cell; (ii) a second nucleic acid construct comprising a second nucleic acid sequence encoding the recombinant polypeptide of interest; a third nucleic acid sequence encoding an orthogonal tRNA synthetase, a fourth nucleic acid sequence encoding an orthogonal tRNA interactable with the tRNA synthetase; and (iv) a promoter operably attached to the first, second, third and/or fourth nucleic acid sequences so as to direct expression of the first nucleic acid sequence, the second nucleic acid sequence, the third nucleic acid sequence and/or the fourth nucleic acid sequence in the auxotrophic host cell. In addition, the method comprises b) subjecting the auxotrophic host cell to a medium that lacks the first metabolite and/or comprises a non-natural amino acid under conditions such that the second nucleic acid is expressed to produce the recombinant polypeptide having the non-natural amino acid incorporated therein.

In an alternative embodiment, the first, second, third and fourth nucleic acid sequences are all contained on the same construct.

Preferably, the expression system is capable of expressing the target polypeptide at a total productivity of polypeptide of at least 1 g/L to at least 80 g/L. In a particular embodiment, the recombinant polypeptide is expressed at a level of at least 3 g/L, 4 g/L, 5 g/L, 6 g/L, 7 g/L, 8 g/L, 9 g/L, 10 g/L, 12 g/L, 15 g/L, 20 g/L, 25 gL, 30 g/L, 35 g/L, 40 g/L, 45 g/L, 50 g/L, 60 g/L, 70 g/L, or at least 80 g/L.

In one embodiment, at least one recombinant polypeptide can be expressed in a cell that is auxotrophic for one metabolite, wherein the auxotrophy serves as a selection marker for the maintenance of the nucleic acid expression vector encoding the polypeptide of interest and the prototrophy-enabling enzyme. Alternatively, more than one recombinant polypeptide can be expressed in a cell that is auxotrophic for one metabolite, wherein the nucleic acids encoding the recombinant polypeptides can be contained on the same vector, or alternatively, on multiple vectors.

In yet another embodiment, more than one expression vector encoding different target polypeptides can be maintained in a host cell auxotrophic for at least one metabolite, wherein one expression vector contains a nucleic acid encoding a prototrophic-enabling enzyme and a first target polypeptide of interest, and a second expression vector contains a nucleic acid encoding an alternative, non-auxotrophic selection marker and a second polypeptide of interest.

In another embodiment, at least one recombinant polypeptide can be expressed in a cell that is auxotrophic for more than one metabolite, wherein the multiple auxotrophies serve as selection markers for the maintenance of nucleic acid expression vectors. For example, an expression vector may be utilized in which a first and second prototrophy-enabling selection marker gene are present. If both marker genes are located on the same DNA construct, the host cell containing the construct may be maintained under either or both of the conditions in which host cell survival requires the presence of the selection marker gene(s). When only one of the marker-gene dependent survival conditions is present, the corresponding marker gene must be expressed, and the other marker gene(s) can then be either active or inactive, though all necessary nutrients for which the cell remains auxotrophic will still be supplied by the medium. This permits the same target gene, or the same set of covalently linked target genes, encoding the desired transgenic product(s) and/or desired transgenic activity(ies), to be maintained in the host cell continuously as the host cell is transitioned between or among different conditions. If each of the two selection marker genes is located on a different DNA construct, then, in order to maintain both of the DNA constructs in the host cell, both of the marker-gene dependent survival conditions must be present, and both of the corresponding marker gene must be expressed. This permits more than one non-covalently linked target gene or set of target gene(s) to be separately maintained in the host cell. The coding sequence of each of the chosen selection marker genes independently can be operably attached to either a constitutive or a regulated promoter.

Dual-target-gene examples of such a multi-target-gene system include, but are not limited to: (1) systems in which the expression product of one of the target genes interacts with the other target gene itself; (2) systems in which the expression product of one of the target genes interacts with the other target gene's expression product, e.g., a protein and its binding protein or the α and β polypeptides of an α and β protein; (3) systems in which the two expression products of the two genes both interact with a third component, e.g., a third component present in the host cell; (4) systems in which the two expression products of the two genes both participate in a common biocatalytic pathway; and (5) systems in which the two expression products of the two genes function independently of one another, e.g., a bi-clonal antibody expression system.

In one example of a dual-target-gene system of the above-listed type (1), a first target gene can encode a desired target protein, wherein the first target gene is under the control of a regulated promoter; the second target gene may then encode a protein involved in regulating the promoter of the first target gene, e.g., the second target gene may encode the first target gene's promoter activator or repressor protein. In an example in which the second gene encodes a promoter regulatory protein for the first gene, the coding sequence of the second gene can be under the control of a constitutive promoter. In one embodiment, the second gene will be part of a separate DNA construct that is a maintained in the cell as a high-copy-number construct with a copy number of at least 10, 20, 30, 40, 50, or more than 50 copies being maintained in the host cell.

Transformation

Transformation of the auxotrophic host cells with the vector(s) may be performed using any transformation methodology known in the art, and bacterial host cells may be transformed as intact cells or as protoplasts (i.e. including cytoplasts). Exemplary transformation methodologies include poration methodologies, e.g., electroporation, protoplast fusion, bacterial conjugation, and divalent cation treatment, e.g., calcium chloride treatment or CaCl/Mg-.sup.2+ treatment, or other well known methods in the art. See, e.g., Morrison, J. Bact., 132:349-351 (1977); Clark-Curtiss & Curtiss, Methods in Enzymology, 101:347-362 (Wu et al., eds, 1983), Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994)).

Selection

Preferably, cells that are not successfully transformed are selected against following transformation, and continuously during the fermentation. The selection marker can be an auxotrophic selection marker and/or a traditional antibiotic selection marker. In a specific embodiment, the selection marker is an auxotrophic marker. When the cell is auxotrophic for multiple nutrient compounds, the auxotrophic cell can be grown on medium supplemented with all of those nutrient compounds until transformed with the prototrophy-restoring vector. Where the host cell is or has been made defective for multiple biosynthetic activities, the prototrophy-restorative marker system(s) can be selected to restore one or more or all of the biosynthetic activities, with the remainder being compensated for by continuing to provide, in the medium, the still-lacking nutrients. In selection marker systems in which more than one biosynthetic activity, and/or more than one prototrophy, is restored, the plurality of selection marker genes may be expressed together on one vector or may be co-expressed separately on different vectors. Even where a single metabolite is the target of the selection marker system, multiple biosynthetic activities may be involved in the selection marker system. For example, two or more genes encoding activities from the same anabolic pathway may be expressed together on one vector or may be co-expressed separately on different vectors, in order to restore prototrophy in regard to biosynthesis of the compound that is the product of the pathway.

Where the selection marker is an antibiotic resistance gene, the associated antibiotic can be added to the medium to select against non transformed and revertant cells, as well known in the art.

Fermentation

As used herein, the term "fermentation" includes both embodiments in which literal fermentation is employed and embodiments in which other, non-fermentative culture modes are employed. Fermentation may be performed at any scale. In one embodiment, the fermentation medium may be selected from among rich media, minimal media, a mineral salts media; a rich medium may be used, but is preferably avoided. In another embodiment either a minimal medium or a mineral salts medium is selected. In still another embodiment, a minimal medium is selected. In yet another embodiment, a mineral salts medium is selected. Mineral salts media are particularly preferred.

Prior to transformation of the host cell with a nucleic acid construct encoding a prototrophic enabling enzyme, the host cell can be maintained in a media comprising a supplemental metabolite, or analogue thereof, which complements the auxotrophy. Following transformation, the host cell can be grown in a media that is lacking the complementary metabolite for which the host cell is auxotrophic. In this way, host cells that do not contain the selection marker enabling prototrophy are selected against. Mineral salts media consists of mineral salts and a carbon source such as, e.g., glucose, sucrose, or glycerol. Examples of mineral salts media include, e.g., M9 medium, Pseudomonas medium (ATCC 179), Davis and Mingioli medium (see, B D Davis & E S Mingioli, in J. Bact. 60:17-28 (1950)). The mineral salts used to make mineral salts media include those selected from among, e.g., potassium phosphates, ammonium sulfate or chloride, magnesium sulfate or chloride, and trace minerals such as calcium chloride, borate, and sulfates of iron, copper, manganese, and zinc. No organic nitrogen source, such as peptone, tryptone, amino acids, or a yeast extract, is included in a mineral salts medium. Instead, an inorganic nitrogen source is used and this may be selected from among, e g, ammonium salts, aqueous ammonia, and gaseous ammonia. A particular mineral salts medium will contain glucose as the carbon source. In comparison to mineral salts media, minimal media can also contain mineral salts and a carbon source, but can be supplemented with, e.g., low levels of amino acids, vitamins, peptones, or other ingredients, though these are added at very minimal levels.

In one embodiment, media can be prepared using the components listed below. The components can be added in the following order: first (NH4)HPO4, KH2PO4 and citric acid can be dissolved in approximately 30 liters of distilled water; then a solution of trace elements can be added, followed by the addition of an antifoam agent, such as Ucolub N 115. Then, after heat sterilization (such as at approximately 121 degrees C.), sterile solutions of glucose MgSO4 and thiamine-HCl can be added. Control of pH at approximately 6.8 can be achieved using aqueous ammonia. Sterile distilled water can then be added to adjust the initial volume to 371 minus the glycerol stock (123 mL). The chemicals are commercially available from various suppliers, such as Merck. This media can allow for high cell density cultivation (HCDC) for growth of Pseudomonas species and related bacteria. The HCDC can start as a batch process which is followed by two-phase fed-batch cultivation. After unlimited growth in the batch part, growth can be controlled at a reduced specific growth rate over a period of 3 doubling times in which the biomass concentration can increased several fold. Further details of such cultivation procedures is described by Riesenberg, D.; Schulz, V.; Knorre, W. A.; Pohl, H. D.; Korz, D.; Sanders, E. A.; Ross, A.; Deckwer, W. D. (1991) "High cell density cultivation of Escherichia coli at controlled specific growth rate" J Biotechnol: 20(1) 17-27.

The expression system according to the present invention can be cultured in any fermentation format. For example, batch, fed-batch, semi-continuous, and continuous fermentation modes may be employed herein.

The expression systems according to the present invention are useful for transgene expression at any scale (i.e. volume) of fermentation. Thus, e.g., microliter-scale, centiliter scale, and deciliter scale fermentation volumes may be used; and 1 Liter scale and larger fermentation volumes can be used. In one embodiment, the fermentation volume will be at or above 1 Liter. In another embodiment, the fermentation volume will be at or above 5 Liters, 10 Liters, 15 Liters, 20 Liters, 25 Liters, 50 Liters, 75 Liters, 100 Liters, 200 Liters, 50 Liters, 1,000 Liters, 2,000 Liters, 5,000 Liters, 10,000 Liters or 50,000 Liters.

In the present invention, growth, culturing, and/or fermentation of the transformed host cells is performed within a temperature range permitting survival of the host cells, preferably a temperature within the range of about 4O C to about 55O C., inclusive.

In various embodiments, the auxotrophic host cells are grown in high cell densities, as stated in terms of biomass per volume, the biomass being measured as dry cell weight.

In one embodiment, the cell density will be at least 20 g/L. In another embodiment, the cell density will be at least 25 g/L, 30 g/L, 35 g/L, 40 g/L, 45 g/L, 50 g/L, 60 g/L, 70 g/L 80 g/L, 90 g/L, 100 g/L, 110 g/L, 120 g/L, 130 g/L, 140 g/L, or at least 150 g/L.

In another embodiments, the cell density at induction will be between 20 g/L and 150 g/L; 20 g/L and 120 g/L; 20 g/L and 80 g/L; 25 g/L and 80 g/L; 30 g/L and 80 g/L; 35 g/L and 80 g/L; 40 g/L and 80 g/L; 45 g/L and 80 g/L; 50 g/L and 80 g/L; 50 g/L and 75 g/L; 50 g/L and 70 g/L; 40 g/L and 80 g/L.

Improved Expression of Recombinant Protein

The methods of the invention may lead to increased production of the recombinant polypeptide of interest within the auxotrophic host cell. The increased production alternatively can be an increased level of properly processed protein or polypeptide per gram of protein produced, or per gram of host protein. The increased production can also be an increased level of recoverable protein or polypeptide produced per gram of recombinant or per gram of host cell protein. The increased production can also be any combination of an increased level of total protein, increased level of properly processed protein, or increased level of active or soluble protein. In this embodiment, the term "increased" is relative to the level of protein or polypeptide that is produced, properly processed, soluble, and/or recoverable when the protein or polypeptide of interest is expressed in an expression system that utilizes antibiotic selection markers, or in an antibiotic or auxotrophic selection system in the absence of an analogue of the metabolite for which the cell is auxotrophic.

An improved expression of a protein or polypeptide of interest can also refer to an increase in the solubility of the protein. The protein or polypeptide of interest can be produced and recovered from the cytoplasm, periplasm or extracellular medium of the host cell. The protein or polypeptide can be insoluble or soluble. The protein or polypeptide can include one or more targeting sequences or sequences to assist purification, as known in the art.

The term "soluble" as used herein means that the protein is not precipitated by centrifugation at between approximately 5,000 and 20,000× gravity when spun for 10-30 minutes in a buffer under physiological conditions. Soluble proteins are not part of an inclusion body or other precipitated mass. Similarly, "insoluble" means that the protein or polypeptide can be precipitated by centrifugation at between 5,000 and 20,000× gravity when spun for 10-30 minutes in a buffer under physiological conditions. Insoluble proteins or polypeptides can be part of an inclusion body or other precipitated mass. The term "inclusion body" is meant to include any intracellular body contained within a cell wherein an aggregate of proteins or polypeptides has been sequestered.

The methods of the invention can produce protein localized to the periplasm of the host cell. In one embodiment, the method produces properly processed proteins or polypeptides of interest in the cell. In another embodiment, the expression of the recombinant polypeptide may produce active proteins or polypeptides of interest in the cell.

In one embodiment, the method produces at least 0.1 g/L correctly processed protein. A correctly processed protein has an amino terminus of the native protein. In some embodiments, at least 50% of the protein or polypeptide of interest comprises a native amino terminus. In another embodiment, at least 60%, at least 70%, at least 80%, at least 90%, or more of the protein has an amino terminus of the native protein. In various embodiments, the method produces 0.1 to 10 g/L correctly processed protein in the cell, including at least about 0.2, about 0.3, about 0.4, about 0.5, about 0.6, about 0.7, about 0.8, about 0.9 or at least about 1.0 g/L correctly processed protein. In another embodiment, the total correctly processed protein or polypeptide of interest produced is at least 1.0 g/L, at least about 2 g/L, at least about 3 g/L, about 4 g/L, about 5 g/L, about 6 g/L, about 7 g/L, about 8 g/L, about 10 g/L, about 15 g/L, about 20 g/L, about 25 g/L, about 30 g/L, about 35 g/l, about 40 g/l, about 45 g/l, at least about 50 g/L, or greater. In some embodiments, the amount of correctly processed protein produced is at least about 5%, about 10%, about 15%, about 20%, about 25%, about 30%, about 40%, about 50%, about 60%, about 70%, about 80%, about 90%, about 95%, about 96%, about 97%, about 98%, at least about 99%, or more of total recombinant protein in a correctly processed form.

The methods of the invention can also lead to increased yield of the protein or polypeptide of interest. In one embodiment, the method produces a protein or polypeptide of interest as at least about 5%, at least about 10%, about 15%, about 20%, about 25%, about 30%, about 40%, about 45%, about 50%, about 55%, about 60%, about 65%, about 70%, about 75%, or greater of total cell protein (tcp). "Percent total cell protein" is the amount of protein or polypeptide in the host cell as a percentage of aggregate cellular protein. The determination of the percent total cell protein is well known in the art.

In a particular embodiment, the host cell can have a recombinant polypeptide, polypeptide, protein, or fragment thereof expression level of at least 1% tcp and a cell density of at least 40 g/L, when grown (i.e. within a temperature range of about 4° C. to about 55° C., including about 10° C., about 15° C., about 20° C., about 25° C., about 30° C., about 35° C., about 40° C., about 45° C., and about 50° C.) in a mineral salts medium. In a particularly preferred embodiment, the expression system will have a protein or polypeptide expression level of at least 5% tcp and a cell density of at least 40 g/L, when grown (i.e. within a temperature range of about 4° C. to about 55° C., inclusive) in a mineral salts medium at a fermentation scale of at least about 10 Liters.

In some embodiments, the protein can also be produced in an active form. The term "active" means the presence of biological activity, wherein the biological activity is comparable or substantially corresponds to the biological activity of a corresponding native protein or polypeptide. In the context of proteins this typically means that a polynucleotide or polypeptide comprises a biological function or effect that has at least about 20%, about 50%, preferably at least about 60-80%, and most preferably at least about 90-95% activity compared to the corresponding native protein or polypeptide using standard parameters. The determination of protein or polypeptide activity can be performed utilizing corresponding standard, targeted comparative biological assays for particular proteins or polypeptides. One indication that a protein or polypeptide of interest maintains biological activity is that the polypeptide is immunologically cross reactive with the native polypeptide.

The invention can also improve recovery of active protein or polypeptide of interest. Active proteins can have a specific activity of at least about 20%, at least about 30%, at least about 40%, about 50%, about 60%, at least about 70%, about 80%, about 90%, or at least about 95% that of the native protein or polypeptide that the sequence is derived from. Further, the substrate specificity (kcat/Km) is optionally substantially similar to the native protein or polypeptide. Typically, kcat/Km will be at least about 30%, about 40%, about 50%, about 60%, about 70%, about 80%, at least about 90%, at least about 95%, or greater. Methods of assaying and quantifying measures of protein and polypeptide activity and substrate specificity (kcat/Km), are well known to those of skill in the art.

Isolation and Purification

The recombinant proteins produced according to this invention may be isolated and purified to substantial purity by standard techniques well known in the art, including, but not limited to, ammonium sulfate or ethanol precipitation, acid extraction, anion or cation exchange chromatography, phosphocellulose chromatography, hydrophobic interaction chromatography, affinity chromatography, nickel chromatography, hydroxylapatite chromatography, reverse phase chromatography, lectin chromatography, preparative electrophoresis, detergent solubilization, selective precipitation with such substances as column chromatography, immunopurification methods, and others. For example, proteins having established molecular adhesion properties can be reversibly fused a ligand. With the appropriate ligand, the protein can be selectively adsorbed to a purification column and then freed from the column in a relatively pure form.

The fused protein is then removed by enzymatic activity. In addition, protein can be purified using immunoaffinity columns or Ni-NTA columns. General techniques are further described in, for example, R. Scopes, Protein Purification: Principles and Practice, Springer-Verlag: N.Y. (1982); Deutscher, Guide to Protein Purification, Academic Press (1990); U.S. Pat. No. 4,511,503; S. Roe, Protein Purification Techniques: A Practical Approach (Practical Approach Series), Oxford Press (2001); D. Bollag, et al., Protein Methods, Wiley-Lisa, Inc. (1996); A K Patra et al., Protein Expr Purif, 18(2): p/182-92 (2000); and R. Mukhija, et al., Gene 165(2): p. 303-6 (1995). See also, for example, Ausubel, et al. (1987 and periodic supplements); Deutscher (1990) "Guide to Protein Purification," Methods in Enzymology vol. 182, and other volumes in this series; Coligan, et al. (1996 and periodic Supplements) Current Protocols in Protein Science Wiley/Greene, NY; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See also, for example, Hochuli (1989) Chemische Industrie 12:69-70; Hochuli (1990) "Purification of Recombinant Proteins with Metal Chelate Absorbent" in Setlow (ed.) Genetic Engineering, Principle and Methods 12:87-98, Plenum Press, NY; and Crowe, et al. (1992) QIAexpress: The High Level Expression & Protein Purification System QIAGEN, Inc., Chatsworth, Calif.

Detection of the expressed protein is achieved by methods known in the art and includes, for example, radioimmunoassays, Western blotting techniques or immunoprecipitation.

The recombinantly produced and expressed enzyme can be recovered and purified from the recombinant cell cultures by numerous methods, for example, high performance liquid chromatography (HPLC) can be employed for final purification steps, as necessary.

Certain proteins expressed in this invention may form insoluble aggregates ("inclusion bodies"). Several protocols are suitable for purification of proteins from inclusion bodies. For example, purification of inclusion bodies typically involves the extraction, separation and/or purification of inclusion bodies by disruption of the host cells, e.g., by incubation in a buffer of 50 mM TRIS/HCL pH 7.5, 50 mM NaCl, 5 mM MgCl.sub.2, 1 mM DTT, 0.1 mM ATP, and 1 mM PMSF. The cell suspension is typically lysed using 2-3 passages through a French Press. The cell suspension can also be homogenized using a Polytron (Brinknan Instruments) or sonicated on ice. Alternate methods of lysing bacteria are apparent to those of skill in the art (see, e.g., Sambrook et al., supra; Ausubel et al., supra).

If necessary, the inclusion bodies can be solubilized, and the lysed cell suspension typically can be centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art.

Alternatively, it is possible to purify the recombinant proteins or peptides from the host periplasm. After lysis of the host cell, when the recombinant protein is exported into the periplasm of the host cell, the periplasmic fraction of the bacteria can be isolated by cold osmotic shock in addition to other methods known to those skilled in the art. To isolate recombinant proteins from the periplasm, for example, the bacterial cells can be centrifuged to form a pellet. The pellet can be resuspended in a buffer containing 20% sucrose. To lyse the cells, the bacteria can be centrifuged and the pellet can be resuspended in ice-cold 5 mM MgSO4 and kept in an ice bath for approximately 10 minutes. The cell suspension can be centrifuged and the supernatant decanted and saved. The recombinant proteins present in the supernatant can be separated from the host proteins by standard separation techniques well known to those of skill in the art.

An initial salt fractionation can separate many of the unwanted host cell proteins (or proteins derived from the cell culture media) from the recombinant protein of interest. One such example can be ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

The molecular weight of a recombinant protein can be used to isolated it from proteins of greater and lesser size using ultrafiltration through membranes of different pore size (for example, Amicon or Millipore membranes). As a first step, the protein mixture can be ultrafiltered through a membrane with a pore size that has a lower molecular weight cut-off than the molecular weight of the protein of interest. The retentate of the ultrafiltration can then be ultrafiltered against a membrane with a molecular cut off greater than the molecular weight of the protein of interest. The recombinant protein will pass through the membrane into the filtrate. The filtrate can then be chromatographed as described below.

Recombinant proteins can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Renaturation and Refolding

In some embodiments of the present invention, more than 50% of the expressed, transgenic polypeptide, polypeptide, protein, or fragment thereof produced can be produced in a renaturable form in a host cell. In another embodiment about 60%, 70%, 75%, 80%, 85%, 90%, 95% of the expressed protein is obtained in or can be renatured into active form.

Insoluble protein can be renatured or refolded to generate secondary and tertiary protein structure conformation. Protein refolding steps can be used, as necessary, in completing configuration of the recombinant product. Refolding and renaturation can be accomplished using an agent that is known in the art to promote dissociation/association of proteins. For example, the protein can be incubated with dithiothreitol followed by incubation with oxidized glutathione disodium salt followed by incubation with a buffer containing a refolding agent such as urea.

The protein or polypeptide of interest can also be renatured, for example, by dialyzing it against phosphate-buffered saline (PBS) or 50 mM Na-acetate, pH 6 buffer plus 200 mM NaCl. Alternatively, the protein can be refolded while immobilized on a column, such as the Ni NTA column by using a linear 6M-1M urea gradient in 500 mM NaCl, 20% glycerol, 20 mM Tris/HCl pH 7.4, containing protease inhibitors. The renaturation can be performed over a period of 1.5 hours or more. After renaturation the proteins can be eluted by the addition of 250 mM imidazole. Imidazole can be removed by a final dialyzing step against PBS or 50 mM sodium acetate pH 6 buffer plus 200 mM NaCl. The purified protein can be stored at 4° C. or frozen at −80° C.

Other methods include, for example, those that may be described in M H Lee et al., Protein Expr. Purif., 25(1): p. 166-73 (2002), W. K. Cho et al., J. Biotechnology, 77(2-3): p. 169-78 (2000), Ausubel, et al. (1987 and periodic supplements), Deutscher (1990) "Guide to Protein Purification," Methods in Enzymology vol. 182, and other volumes in this series, Coligan, et al. (1996 and periodic Supplements) Current Protocols in Protein Science Wiley/Greene, NY, S. Roe, Protein Purification Techniques: A Practical Approach (Practical Approach Series), Oxford Press (2001); D. Bollag, et al., Protein Methods, Wiley-Lisa, Inc. (1996)

Recombinant Polypeptides

The present invention provides improved protein production in protein expression systems. Examples of recombinant polypeptides that can be used in the present invention include polypeptides derived from prokaryotic and eukaryotic organisms. Such organisms include organisms from the domain Archea, Bacteria, Eukarya, including organisms from the Kingdom Protista, Fungi, Plantae, and Animalia.

The recombinant peptides to be expressed by according to the present invention can be expressed from polynucleotides in which the target polypeptide coding sequence is operably attached to transcription and translation regulatory elements to form a functional gene from which the host cell can express the protein or peptide. The coding sequence can be a native coding sequence for the target polypeptide, if available, but will more preferably be a coding sequence that has been selected, improved, or optimized for use in the selected expression host cell. The gene(s) that result will have been constructed within or will be inserted into one or more vector, which will then be transformed into the expression host cell. Nucleic acid or a polynucleotide said to be provided in an "expressible form" means nucleic acid or a polynucleotide that contains at least one gene that can be expressed by the selected bacterial expression host cell.

Extensive sequence information required for molecular genetics and genetic engineering techniques is widely publicly available. Access to complete nucleotide sequences of mammalian, as well as human, genes, cDNA sequences, amino acid sequences and genomes can be obtained from GenBank at the URL address www.ncbi nlm nih.gov/Entrez. Additional information can also be obtained from GeneCards, an electronic encyclopedia integrating information about genes and their products and biomedical applications from the Weizmann Institute of Science Genome and Bioinformatics (http:/Ibioinformatics.weizmann ac it/cards/), nucleotide sequence information can be also obtained from the EMBL Nucleotide Sequence Database (www.ebi.ac.uk/embl/) or the DNA Databank or Japan (DDBJ, www.ddbi.nig.ac.jp/; additional sites for information on amino acid sequences include Georgetown's protein information resource website (www-nbrf.georgetown.edu/pir/) and Swiss-Prot (au.expasy.org/sprot/sprot-top.html).

The methods and compositions of the present invention are useful for producing high levels of properly processed protein or polypeptide of interest in a cell expression system. The protein or polypeptide of interest (also referred to herein as "target protein" or "target polypeptide") can be of any species and of any size. However, in certain embodiments, the protein or polypeptide of interest is a therapeutically useful protein or polypeptide. In some embodiments, the protein can be a mammalian protein, for example a human protein, and can be, for example, a growth factor, a cytokine, a chemokine or a blood protein. The protein or polypeptide of interest can be processed in a similar manner to the native protein or polypeptide. In certain embodiments, the protein or polypeptide does not include a secretion signal in the coding sequence. In certain embodiments, the protein or polypeptide of interest is less than 100 kD, less than 50 kD, or less than 30 kD in size. In certain embodiments, the protein or polypeptide of interest is a polypeptide of at least about 5, 10, 15, 20, 30, 40, 50 or 100 amino acids.

Extensive sequence information required for molecular genetics and genetic engineering techniques is widely publicly available. Access to complete nucleotide sequences of mammalian, as well as human, genes, cDNA sequences, amino acid sequences and genomes can be obtained from GenBank at the website //www.ncbi.nlm.nih.gov/Entrez. Additional information can also be obtained from GeneCards, an electronic encyclopedia integrating information about genes and their products and biomedical applications from the Weizmann Institute of Science Genome and Bioinformatics (bioinformatics.weizmann ac it/cards), nucleotide sequence information can be also obtained from the EMBL Nucleotide Sequence Database (www.ebi.ac.uk/embl/) or the DNA Databank or Japan (DDBJ, www.ddbi.nig.ac.ii/; additional sites for information on amino acid sequences include Georgetown's protein information resource website (www-nbrf.Reorgetown.edu/pirl) and Swiss-Prot (au.expasy.org/sprot/sprot-top.html).

Examples of proteins that can be expressed in this invention include molecules such as, e.g., renin, a growth hormone, including human growth hormone; bovine growth hormone; growth hormone releasing factor; parathyroid hormone; thyroid stimulating hormone; lipoproteins; α-1-antitrypsin; insulin A-chain; insulin B-chain; proinsulin; thrombopoietin; follicle stimulating hormone; calcitonin; luteinizing hormone; glucagon; clotting factors such as factor VIIIC, factor IX, tissue factor, and von Willebrands factor; anti-clotting factors such as Protein C; atrial naturietic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; a serum albumin such as human serum albumin; mullerian-inhibiting substance; relaxin A-chain; relaxin B-chain; prorelaxin; mouse gonadotropin-associated polypeptide; a microbial protein, such as beta-lactamase; Dnase; inhibin; activin; vascular endothelial growth factor (VEGF); receptors for hormones or growth factors; integrin; protein A or D; rheumatoid factors; a neurotrophic factor such as brain-derived neurotrophic factor (BDNF), neurotrophin-3, -4, -5, or -6 (NT-3, NT-4, NT-5, or NT-6), or a nerve growth factor such as NGF-β; cardiotrophins (cardiac hypertrophy factor) such as cardiotrophin-1 (CT-1); platelet-derived growth factor (PDGF); fibroblast growth factor such as aFGF and bFGF; epidermal growth factor (EGF); transforming growth factor (TGF) such as TGF-alpha and TGF-β, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; anti-HER-2 antibody; superoxide dismutase; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides.

In certain embodiments, the protein or polypeptide can be selected from IL-1, IL-1a, IL-1b, IL-2, IL-3, IL-4, IL-5, IL-6, IL-7, IL-8, IL-9, IL-10, IL-11, IL-12, IL-12elasti, IL-13, IL-15, IL-16, IL-18, IL-18BPa, IL-23, IL-24, VIP, erythropoietin, GM-CSF, G-CSF, M-CSF, platelet derived growth factor (PDGF), MSF, FLT-3 ligand, EGF, fibroblast growth factor (FGF; e.g., α-FGF (FGF-1), β-FGF (FGF-2), FGF-3, FGF-4, FGF-5, FGF-6, or FGF-7), insulin-like growth factors (e.g., IGF-1, IGF-2); tumor necrosis factors (e.g., TNF, Lymphotoxin), nerve growth factors (e.g., NGF), vascular endothelial growth factor (VEGF); interferons (e.g., IFN-α, IFN-β, IFN-v); leukemia inhibitory factor (LIF); ciliary neurotrophic factor (CNTF); oncostatin M; stem cell factor (SCF); transforming growth factors (e.g., TGF-β, TGF-β1, TGF-β2, TGF-β3); TNF superfamily (e.g., LIGHT/TNFSF14, STALL-1/TNFSF13B (BLy5, BAFF, THANK), TNFalpha/TNFSF2 and TWEAK/TNFSF12); or chemokines (BCA-1/BLC-1, BRAK/Kec, CXCL16, CXCR3, ENA-78/LIX, Eotaxin-1, Eotaxin-2/MPIF-2, Exodus-2/SLC, Fractalkine/Neurotactin, GROalpha/MGSA, HCC-1, I-TAC, Lymphotactin/ATAC/SCM, MCP-1/MCAF, MCP-3, MCP-4, MDC/STCP-1/ABCD-1, MIP-1.quadrature, MIP-1.quadrature, MIP-2.quadrature./GRO.quadrature, MIP-3.quadrature./Exodus/LARC, MIP-3/Exodus-3/ELC, MIP-4/PARC/DC-CK1, PF-4, RANTES, SDF1, TARC, or TECK).

In one embodiment of the present invention, the protein of interest can be a multi-subunit protein or polypeptide. Multisubunit proteins that can be expressed include homomeric and heteromeric proteins. The multisubunit proteins may include two or more subunits, that may be the same or different. For example, the protein may be a homomeric protein comprising 2, 3, 4, 5, 6, 7, 8, 9, 10, 11, 12 or more subunits. The protein also may be a heteromeric protein including 2, 3, 4, 5, 6, 7, 8, 9, 10, 11, 12, or more subunits. Exemplary multisubunit proteins include: receptors including ion channel receptors; extracellular matrix proteins including chondroitin; collagen; immunomodulators including MHC proteins, full chain antibodies, and antibody fragments; enzymes including RNA polymerases, and DNA polymerases; and membrane proteins.

In another embodiment, the protein of interest can be a blood protein. The blood proteins expressed in this embodiment include but are not limited to carrier proteins, such as albumin, including human and bovine albumin, transferrin, recombinant transferrin half-molecules, haptoglobin, fibrinogen and other coagulation factors, complement components, immunoglobulins, enzyme inhibitors, precursors of substances such as angiotensin and bradykinin, insulin, endothelin, and globulin, including alpha, beta, and gamma-globulin, and other types of proteins, polypeptides, and fragments thereof found primarily in the blood of mammals. The amino acid sequences for numerous blood proteins have been reported (see, S. S. Baldwin (1993) Comp. Biochem Physiol. 106b:203-218), including the amino acid sequence for human serum albumin (Lawn, L. M., et al. (1981) Nucleic Acids Research, 9:6103-6114.) and human serum transferrin (Yang, F. et al. (1984) Proc. Natl. Acad. Sci. USA 81:2752-2756).

In another embodiment, the protein of interest can be a recombinant enzyme or co-factor. The enzymes and co-factors expressed in this embodiment include but are not limited to aldolases, amine oxidases, amino acid oxidases, aspartases, B12 dependent enzymes, carboxypeptidases, carboxyesterases, carboxylyases, chemotrypsin, CoA requiring enzymes, cyanohydrin synthetases, cystathione synthases, decarboxylases, dehydrogenases, alcohol dehydrogenases, dehydratases, diaphorases, dioxygenases, enoate reductases, epoxide hydrases, fumerases, galactose oxidases, glucose isomerases, glucose oxidases, glycosyltrasferases, methyltransferases, nitrile hydrases, nucleoside phosphorylases, oxidoreductases, oxynitilases, peptidases, glycosyltrasferases, peroxidases, enzymes fused to a therapeutically active polypeptide, tissue plasminogen activator; urokinase, reptilase, streptokinase; catalase, superoxide dismutase; Dnase, amino acid hydrolases (e.g., asparaginase, amidohydrolases); carboxypeptidases; proteases, trypsin, pepsin, chymotrypsin, papain, bromelain, collagenase; neuramimidase; lactase, maltase, sucrase, and arabinofuranosidases.

In another embodiment, the protein of interest can be a single chain, Fab fragment and/or full chain antibody or fragments or portions thereof. A single-chain antibody can include the antigen-binding regions of antibodies on a single stably-folded polypeptide chain. Fab fragments can be a piece of a particular antibody. The Fab fragment can contain the antigen binding site. The Fab fragment can contain 2 chains: a light chain and a heavy chain fragment. These fragments can be linked via a linker or a disulfide bond.

In certain embodiments, the protein of interest is, or is substantially homologous to, a native protein, such as a native mammalian or human protein. In these embodiments, the protein is not found in a concatameric form, but is linked only to a secretion signal and optionally a tag sequence for purification and/or recognition.

Orthogonal Aminoacyl-TRNA Synthetases (O-RS)

As described above, embodiments of the invention include nucleic acid constructs that are engineered to express orthogonal tRNAs and orthogonal tRNA synthetases that allow for the introduction of a non-natural amino acid into a recombinant polypeptide of interested. In order to specifically incorporate an non-natural amino acid in to a protein or polypeptide of interest, in a cell, the substrate specificity of the synthetase is altered so that only the desired non-natural amino acid, but not any of the common 20 amino acids are charged to the tRNA. If the orthogonal synthetase is promiscuous, it will result in mutant proteins with a mixture of natural and non-natural amino acids at the target position.

Certain embodiments of the invention utilize compositions of, and methods of, producing orthogonal aminoacyl-tRNA synthetases that have modified substrate specificity for a specific non-natural amino acid.

A cell that includes an orthogonal aminoacyl-tRNA synthetase (O-RS) is a feature of the invention. The O-RS preferentially aminoacylates an orthogonal tRNA (O-tRNA) with an non-natural amino acid in the cell. In certain embodiments, the O-RS utilizes more than one non-natural amino acid, e.g., two or more, three or more, etc. Thus, an O-RS of the invention can have the capability to preferentially aminoacylate an O-tRNA with different non-natural amino acids. This allows an additional level of control by selecting which non-natural amino acid or combination of non-natural amino acids are put with the cell and/or by selecting the different amounts of non-natural amino acids that are put with the cell for their incorporation.

An O-RS of the invention optionally has one or more improved or enhanced enzymatic properties for the non-natural amino acid as compared to a natural amino acid. These properties include, e.g., higher Km, lower Km, higher kcat, lower kcat, lower kcat/km, higher kcat/km, etc., for the non-natural amino acid, as compared to a naturally occurring amino acid, e.g., one of the 20 known common amino acids.

Optionally, the O-RS can be provided to the cell by a polypeptide that includes an O-RS and/or by a polynucleotide that encodes an O-RS or a portion thereof.

See U.S. Patent Publication Nos. 20100093082 and 20080118464 for additional information on modified ("orthogonal") tRNAs and synthetases.

In one example, a cell comprises an orthogonal aminoacyl-tRNA synthetase (O-RS), an orthogonal tRNA (O-tRNA), an non-natural amino acid, and a nucleic acid that comprises a polynucleotide that encodes a polypeptide of interest, which polynucleotide comprises a selector codon that is recognized by the O-tRNA. Examples of a selector codon contemplated may include, but is not limited to, a stop codon or perhaps four base codon that is associable with the O-tRNA. The recombinant polypeptide may encode for one or more of the selector codons. The O-RS preferentially aminoacylates the orthogonal tRNA (O-tRNA) with the non-natural amino acid in the cell, and the cell produces the polypeptide of interest in the absence of the non-natural amino acid with a yield that is, e.g., less than 30%, less than, 20%, less than 15%, less than 10%, less than 5%, less than 2.5%, etc., of the yield of the polypeptide in the presence of the non-natural amino acid.

Orthogonal tRNAs

Cells that include an orthogonal tRNA (O-tRNA) are utilized by certain embodiments of the invention. The orthogonal tRNA mediates incorporation of an non-natural amino acid into a protein that is encoded by a polynucleotide that comprises a selector codon that is recognized by the O-tRNA, in vivo. In certain embodiments, an O-tRNA of the invention mediates the incorporation of an non-natural amino acid into a protein with, e.g., at least 40%, at least 45%, at least 50%, at least 60%, at least 75%, at least 80%, or even 90% or more as efficiently as tRNA that comprises or is processed in a cell.

Orthogonal TRNA and Orthogonal Aminoacyl-TRNA Synthetase Pairs

An orthogonal pair is composed of an O-tRNA, e.g., a suppressor tRNA, a frameshift tRNA, or the like, and an O-RS. The O-tRNA is not acylated by endogenous synthetases and is capable of mediating incorporation of a non-natural amino acid into a protein that is encoded by a polynucleotide that comprises a selector codon that is recognized by the O-tRNA in vivo. The O-RS recognizes the O-tRNA and preferentially aminoacylates the O-tRNA with an non-natural amino acid in a cell. Methods for producing orthogonal pairs along with orthogonal pairs produced by such methods and compositions of orthogonal pairs for use in cells are included in the invention. The development of multiple orthogonal tRNA/synthetase pairs can allow the simultaneous incorporation of multiple non-natural amino acids using different codons in a cell.

An orthogonal O-tRNA/O-RS pair in a cell can be produced by importing a pair, e.g., a nonsense suppressor pair, from a different organism with inefficient cross species aminoacylation. The O-tRNA and O-RS are efficiently expressed and processed in the cell and the O-tRNA is efficiently exported from the nucleus to the cytoplasm. For example, one such pair is the tyrosyl-tRNA synthetase/tRNA.sub.CUA pair from E. coli (see, e.g., H. M. Goodman, et al., (1968), Nature 217:1019-24; and, D. G. Barker, et al., (1982), FEBS Letters 150:419-23). E. coli tyrosyl-tRNA synthetase efficiently aminoacylates its cognate E. coli tRNA.CUA when both are expressed in the cytoplasm of S. cerevisiae, but does not aminoacylate S. cerevisiae tRNA's. See, e.g., H. Edwards, & P. Schimmel, (1990), Molecular & Cellular Biology 10:1633-41; and, H. Edwards, et al., (1991), PNAS United States of America 88:1153-6. In addition, E. coli tyrosyl tRNA.sub.CUA is a poor substrate for S. cerevisiae aminoacyl-tRNA synthetases (see, e.g., V. Trezeguet, et al., (1991), Molecular & Cellular Biology 11:2744-51), but functions efficiently in protein translation in S. cerevisiae. See, e.g., H. Edwards, & P. Schimmel, (1990) Molecular & Cellular Biology 10:1633-41; H. Edwards, et al., (1991), PNAS United States of America 88:1153-6; and, V. Trezeguet, et al., (1991), Molecular & Cellular Biology 11:2744-51. Moreover, E. coli TyrRS does not have an editing mechanism to proofread an non-natural amino acid ligated to the tRNA.

The O-tRNA and O-RS can be naturally occurring or can be derived by mutation of a naturally occurring tRNA and/or RS, which generates libraries of tRNA's and/or libraries of RSs, from a variety of organism. See the section entitled "Sources and Hosts" herein. In various embodiments, the O-tRNA and O-RS are derived from at least one organism. In another embodiment, the O-tRNA is derived from a naturally occurring or mutated naturally occurring tRNA from a first organism and the O-RS is derived from naturally occurring or mutated naturally occurring RS from a second organism. In one embodiment, the first and second non-vertebrate organisms are the same. Alternatively, the first and second non-vertebrate organisms can be different.

See also, International patent application WO 2002/086075, entitled "Methods and compositions for the production of orthogonal tRNA-aminoacyltRNA synthetase pairs."

The following examples are offered by way of illustration and not by way of limitation.

EXPERIMENTAL EXAMPLES

The methionine auxotrophic P. fluorescens strains DC454, DC485, DC552, DC556 and DC568 (metC deletion) carrying the cytoplasmic-IFN-beta construct pIFN-001 were analyzed as follows. Briefly, single colonies were inoculated in M9 medium supplemented with 1% glucose and trace elements plus methionine (250 ug/mL) and grown overnight at 30 C with shaking. The seed cultures were used to inoculate 200 mL Dow HTP Medium (a defined minimal salts medium with glycerol as carbon source) plus methionine (250 ug/mL) to an OD600 of ~0.1. Flasks were incubated overnight at 30 C with shaking. Following an initial 24-hour growth phase, the cells were collected by centrifugation and resuspended in the same HTP medium without methionine and incubated at 30 C for 30 minutes. Cells were collected by centrifugation and resuspended in 200 mL HTP medium with either methionine (250 ug/mL) or azidohomoalanine (AHA) (1 mg/mL) as the additive and expression via the Ptac promoter was induced with the addition of 0.3 mM isopropyl-β-D-1-thiogalactopyranoside (IPTG). Where appropriate, expression of folding modulator was induced with 1% mannitol. Cultures were sampled at the time of induction (I0), and at 6 (I6), 12 (I12) and 24 hours (I24) post induction. Cell density was measured by optical density at 600 nm (OD600). After centrifugation the cells were resuspended in PBS and cell density was adjusted to OD600=20. Aliquots of 200 μL were transferred to fresh tubes and frozen at −80 C for later processing Soluble and insoluble fractions were prepared by sonication followed by centrifugation. Diluted culture broth samples (400 uL) were thawed and sonicated with a Cell Lysis Automated Sonication System (CLASS, Scinomix) with a 24 probe tip horn. The lysates were centrifuged at 14,000 rpm for 20 minutes (4° C.) and the supernatants collected (soluble fraction). The pellets (insoluble fraction) were frozen and later thawed for processing. Residual supernatant was removed from the pellet by re-centrifugation at 20,800×g for 20 minutes at 4 C. The pellets were then resuspended in phosphate buffered saline (PBS), pH 7.4, by sonication.

Expression of IFN-beta in the methionine auxotrophic strains was evaluated at the 1 L scale (200 mL working volume). Triplicate shake flasks for each of the five strains constructed (see Table 3) were grown and induced as described in Materials and Methods. Two of the shake flasks were used for analysis of AHA incorporation, while the remaining flask was used as a control with methionine as the additive.

The IFN-beta expression strains grew as expected, reaching cell densities of approximately 10 OD600 units after an initial 24 hour growth period, and 15-30 units following a 24 hour induction period. In general, the growth of strains following the addition of AHA and methionine was similar.

Figure 2:
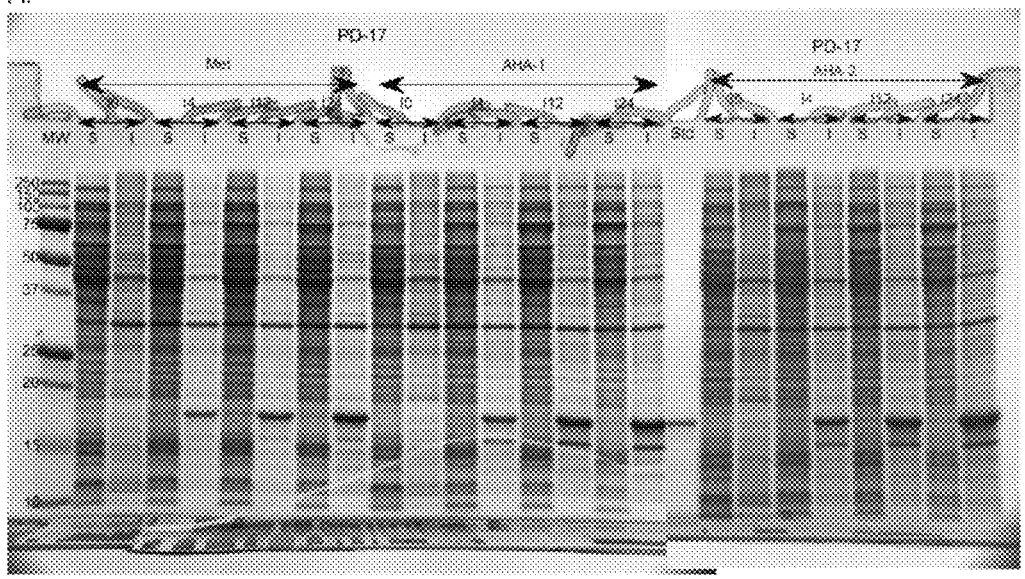
FIG. 2 shows SDS-PAGE (A) and Western Blot (B) analyses of soluble (S) and insoluble (I) protein expressed in PD-17 (DC485) methionine auxotrophic strain carrying pIFN-001. Samples collected at I0, I6, I12 and I24 were normalized to OD600=20. 15 µL of 1:2 diluted normalized samples were loaded in each gel. Standard protein [400 ng (A) and 50 ng (B)] was loaded as a reference. Samples from a methionine-supplemented flask are shown on the left, while samples from flasks supplemented with AHA are shown in the middle and on the right.
Figure 2:
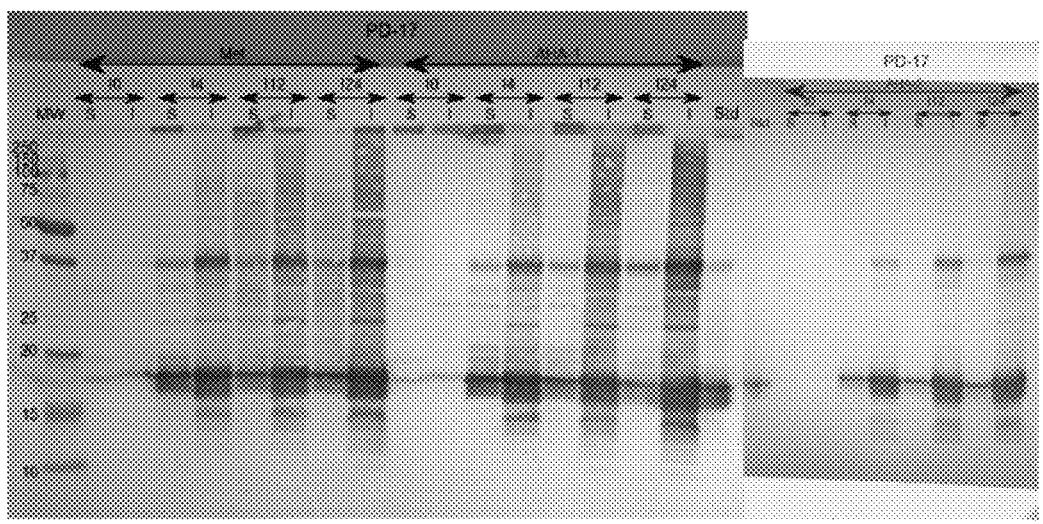

Samples taken at I0, I6, I12 and I24 were normalized to a cell density of 20 OD600 units and fractionated. Protein from both the resulting soluble and insoluble fractions was analyzed by SDS-PAGE and Western blots (example shown in FIG. 2). In all strains, IFN-beta was expressed in the presence of methionine or AHA post-induction and, consistent with observations made in the initial study, the expressed IFN-beta accumulated mainly in the insoluble cellular fraction. The profiles and levels of IFN-beta expression were similar among the strains analyzed. Within each strain, the duplicate flasks with AHA addition gave very similar results. And in the case of WT, FMO-16 and FMO-18, it appeared that more IFN-beta protein was expressed in the AHA-containing samples than in the methionine-containing control sample. Based on SDS-PAGE results, the yield of expressed target protein was estimated to be in the range of 100-300 mg/L culture.

TABLE 3

Shake Flask Numbers of Strains for Analysis of AHA Incorporation

| Flask Number | Host Strain | Host Name | Amino Acid additive |
|---|---|---|---|
| 1 | DC454 | WT | Met |
| 2 | | | AHA |
| 3 | | | AHA |
| 4 | DC485 | PD-17 | Met |
| 5 | | | AHA |
| 6 | | | AHA |

TABLE 3-continued

Shake Flask Numbers of Strains for
Analysis of AHA Incorporation

| Flask Number | Host Strain | Host Name | Amino Acid additive |
|---|---|---|---|
| 7 | DC552 | FMO-16 | Met |
| 8 | | | AHA |
| 9 | | | AHA |
| 10 | DC556 | FMO-12 | Met |
| 11 | | | AHA |
| 12 | | | AHA |
| 13 | DC568 | FMO-18 | Met |
| 14 | | | AHA |
| 15 | | | AHA |

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed is:

1. A method for producing a recombinant polypeptide of interest comprising:
   a) obtaining a population of cells auxotrophic for at least one first metabolite and a second metabolite, wherein said at least one first metabolite is uracil or proline, or both, and said second metabolite is a natural amino acid;
   b) introducing into cells of said population at least one first nucleic acid construct comprising at least one auxotrophic selection marker, wherein said at least one auxotrophic selection marker comprises a pyrF gene or a proC gene, or both, and wherein expression of said at least one auxotrophic selection marker restores prototrophy for the at least one first metabolite;
   c) introducing into cells of said population a: (i) a second nucleic acid sequence encoding said recombinant polypeptide of interest; and (ii) a promoter operably attached to said second nucleic acid sequence so as to direct expression of the second nucleic acid sequence;
   d) subjecting said population of cells to a first medium lacking said first metabolite under conditions such that transformed cells having restored prototrophy for the first metabolite are obtained; and
   e) subjecting said transformed cells to a second medium comprising a non-natural amino acid correlating to said second metabolite under conditions such that said second nucleic acid sequence is expressed to produce said recombinant polypeptide of interest having said non-natural amino acid incorporated therein;
   wherein said first medium and said second medium are the same or different; and
   wherein said second nucleic acid sequence is provided on said first nucleic acid construct or a second nucleic acid construct separate to said first nucleic acid construct.

2. The method of claim 1, wherein the first medium and the second medium are different.

3. The method of claim 1, wherein said first medium and said second medium are the same.

4. The method of claim 1, wherein said population of cells comprises bacterial host cells.

5. The method of claim 4, wherein said bacterial host cells comprise Pseudomonas fluorescens.

6. The method of claim 4, wherein said bacteria host cells comprise E. coli.

7. The method of claim 1, wherein said population of cells lack an expression construct comprising an antibiotic selection marker.

8. The method of claim 1, wherein said first medium lacks an antibiotic.

9. The method of claim 1, wherein said second metabolite comprise methionine.

10. A method for producing a recombinant polypeptide of interest comprising:
    a) introducing into a host cell that is auxotrophic for at least one metabolite, at least one first nucleic acid sequence encoding at least one polypeptide active in the biosynthesis of said at least one metabolite, and wherein expression of said auxotrophic selection marker restores prototrophy for the at least one metabolite to the auxotrophic host cell;
    b) introducing into said host cell: (i) a second nucleic acid sequence encoding said recombinant polypeptide of interest; (ii) a third nucleic acid sequence encoding an orthogonal tRNA synthetase; and (iii) a fourth nucleic acid sequence encoding an orthogonal tRNA; and (iv) a promoter operably attached to said second, third, and/or fourth nucleic acid sequences so as to direct expression of the second nucleic acid, third nucleic acid sequence and/or fourth nucleic acid sequence in said auxotrophic host cell, wherein said second nucleic acid sequence, third nucleic acid sequence or said fourth nucleic acid sequence, or a combination thereof are provided on said first nucleic acid construct; and
    c) subjecting the auxotrophic host cell to a medium that lacks the at least one metabolite under conditions such that said second nucleic acid is expressed to produce said recombinant polypeptide of interest having said non-natural amino acid incorporated therein.

11. The method of claim 10, wherein the second nucleic acid sequence comprises at least one selector codon.

12. The method of claim 10, wherein the at least one metabolite is a nucleoside, nucleotide, nitrogenous base, amino acid or carbon source.

13. The method of claim 10, wherein said first nucleic acid sequence encodes a pyrimidine-type biosynthetic enzyme, a purine-type biosynthetic enzyme, a biosynthetic amino acid enzyme or a utilization enzyme.

14. The method of claim 10, wherein said second nucleic acid sequence is provided on said first nucleic acid construct.

15. The method of claim 10, wherein said third nucleic acid sequence and said fourth nucleic acid sequence are provided on the same or separate constructs but not on said first nucleic acid construct.

16. The method of claim 10, said at least one metabolite comprises uracil or proline, or both.

17. The method of claim 16, wherein said at least on first nucleic acid sequence comprises a pyrF gene or a proC gene, or both.

* * * * *